US012611697B2

(12) United States Patent (10) Patent No.: US 12,611,697 B2
Roy et al. (45) Date of Patent: Apr. 28, 2026

(54) HIGHER BANDWIDTH MICROMACHINED TRANSDUCERS MIXED WITH BIASING SCHEME

(71) Applicant: GE Precision Healthcare LLC, Waukesha, WI (US)

(72) Inventors: Rupak Bardhan Roy, Nice (FR); Omid Farhanieh, Antibes (FR); Alessandro Stuart Savoia, Rome (IT)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 124 days.

(21) Appl. No.: 18/460,440

(22) Filed: Sep. 1, 2023

(65) Prior Publication Data

US 2025/0073750 A1      Mar. 6, 2025

(51) Int. Cl.
B06B 1/02          (2006.01)
A61B 8/00          (2006.01)

(52) U.S. Cl.
CPC .......... B06B 1/0276 (2013.01); A61B 8/4488 (2013.01); A61B 8/54 (2013.01); B06B 1/0292 (2013.01); B06B 2201/51 (2013.01); B06B 2201/76 (2013.01)

(58) Field of Classification Search
None
See application file for complete search history.

(56) References Cited

U.S. PATENT DOCUMENTS 7,745,248 B2    6/2010  Park et al.
8,327,521 B2   12/2012  Dirksen et al.

2003/0048698 A1 *  3/2003  Barnes .................. B06B 1/0292
                                                    367/181
2007/0059858 A1    3/2007  Caronti et al.
2008/0212807 A1 *  9/2008  Wang .................... H04R 17/00
                                                    310/322

(Continued)

FOREIGN PATENT DOCUMENTS

EP          2806983 B1      4/2020
WO      2017216139 A1     12/2017

OTHER PUBLICATIONS

T. Merrien et al, "Lumped-Parameter Equivalent Circuit Modeling of CMUT Array Elements", IEEE Open Journal of Ultrasonics, Ferroelectrics, and Frequency Control, vol. 2, pp. 1-16, Jan. 2022 (Year: 2022).*

(Continued)

*Primary Examiner* — Nyrobi Celestine
(74) *Attorney, Agent, or Firm* — McCoy Russell LLP

(57) ABSTRACT

Various methods and systems are provided for increasing a fractional bandwidth of an ultrasound device, for use in both low and high frequency applications. In one example, where a transducer array includes one or more transducer elements comprising a plurality of capacitive micromachined ultrasound transducers (cMUT), the fractional bandwidth may be advantageously increased by applying different bias voltages to different groupings of cMUTs within each transducer element. A ratio between the different bias voltages may be optimized to maximize the fractional bandwidth. In another example, the different bias voltages may be configured to operate a first grouping of cMUTs in a transmit mode, and a second grouping of cMUTs in a receive mode.

6 Claims, 11 Drawing Sheets

(56) References Cited

U.S. PATENT DOCUMENTS

| | | | |
|---|---|---|---|
| 2010/0268089 A1* | 10/2010 | Degertekin | B06B 1/0292 |
| | | | 600/467 |
| 2016/0047780 A1* | 2/2016 | Shin | B06B 1/0215 |
| | | | 367/7 |
| 2016/0199030 A1* | 7/2016 | Patil | A61B 8/4411 |
| | | | 600/459 |
| 2016/0365840 A1 | 12/2016 | Klee et al. | |
| 2019/0357882 A1* | 11/2019 | Johnson | A61B 8/4281 |
| 2020/0049807 A1* | 2/2020 | Pekar | B06B 1/0292 |
| 2020/0147642 A1* | 5/2020 | Motieian Najar | B06B 1/0622 |
| 2020/0322730 A1* | 10/2020 | Kamiya | B06B 1/0651 |
| 2023/0408663 A1* | 12/2023 | Monsalve Guaracao | |
| | | | G01S 7/527 |

OTHER PUBLICATIONS

Bayram, C. et al., "Bandwidth improvement in a cMUT array with mixed sized elements," Proceedings of the IEEE Ultrasonics Symposium, 2005., Sep. 18, 2005, Rotterdam, Netherlands, 4 pages.

Zhang, X. et al., "Design of high-frequency broadband CMUT arrays," Proceedings of the 2015 IEEE International Ultrasonics Symposium (IUS), Oct. 21, 2015, Taipei, Taiwan, 4 pages.

Kawasaki, S. et al., "Pre-charged collapse-mode capacitive micromachined ultrasonic transducer (CMUT) for broadband ultrasound power transfer," Proceedings of the 2021 IEEE Wireless Power Transfer Conference (WPTC), Jun. 1, 2021, San Diego, California, 6 pages.

Roy, R., "Methods and Systems for Capacitive Micromachined Ultrasonic Transducers," U.S. Appl. No. 18/163,209, filed Feb. 1, 2023, 55 pages.

* cited by examiner

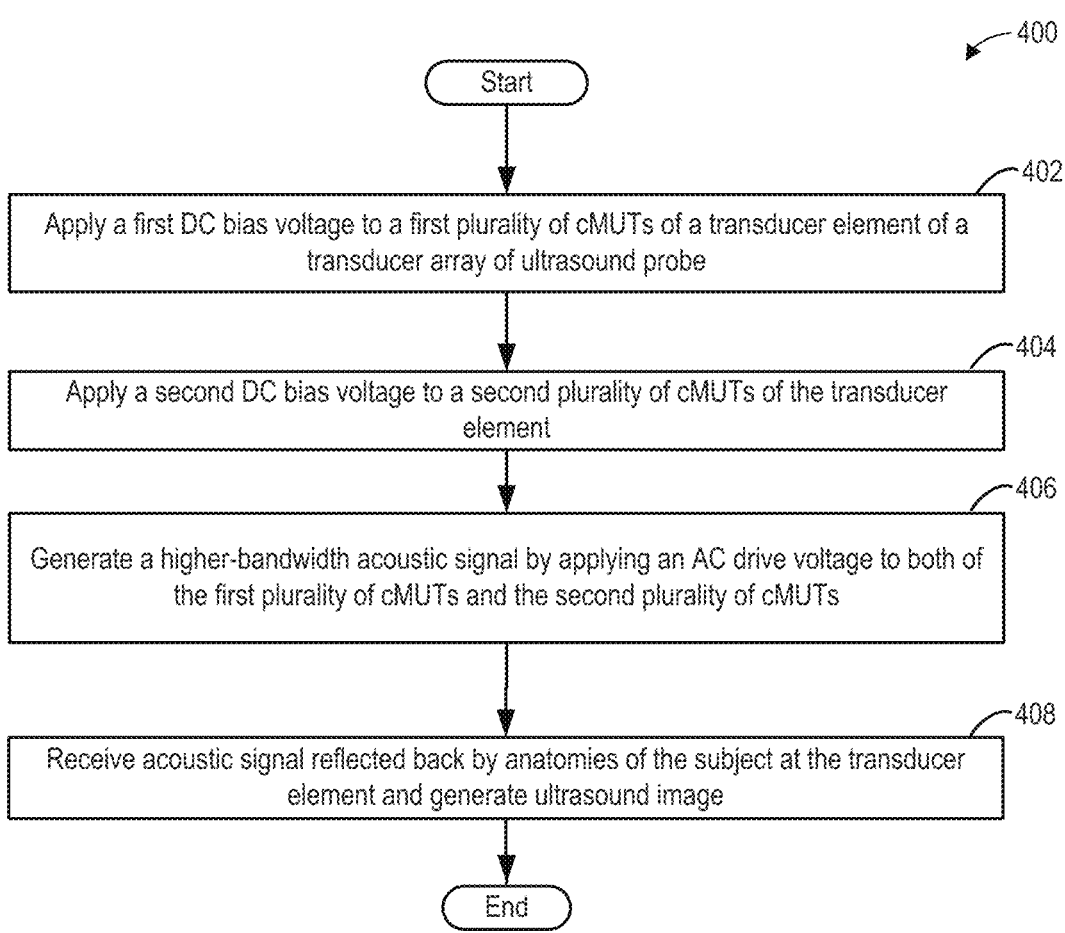

400

Start

402
Apply a first DC bias voltage to a first plurality of cMUTs of a transducer element of a transducer array of ultrasound probe 404
Apply a second DC bias voltage to a second plurality of cMUTs of the transducer element 406
Generate a higher-bandwidth acoustic signal by applying an AC drive voltage to both of the first plurality of cMUTs and the second plurality of cMUTs 408
Receive acoustic signal reflected back by anatomies of the subject at the transducer element and generate ultrasound image End

FIG. 4A

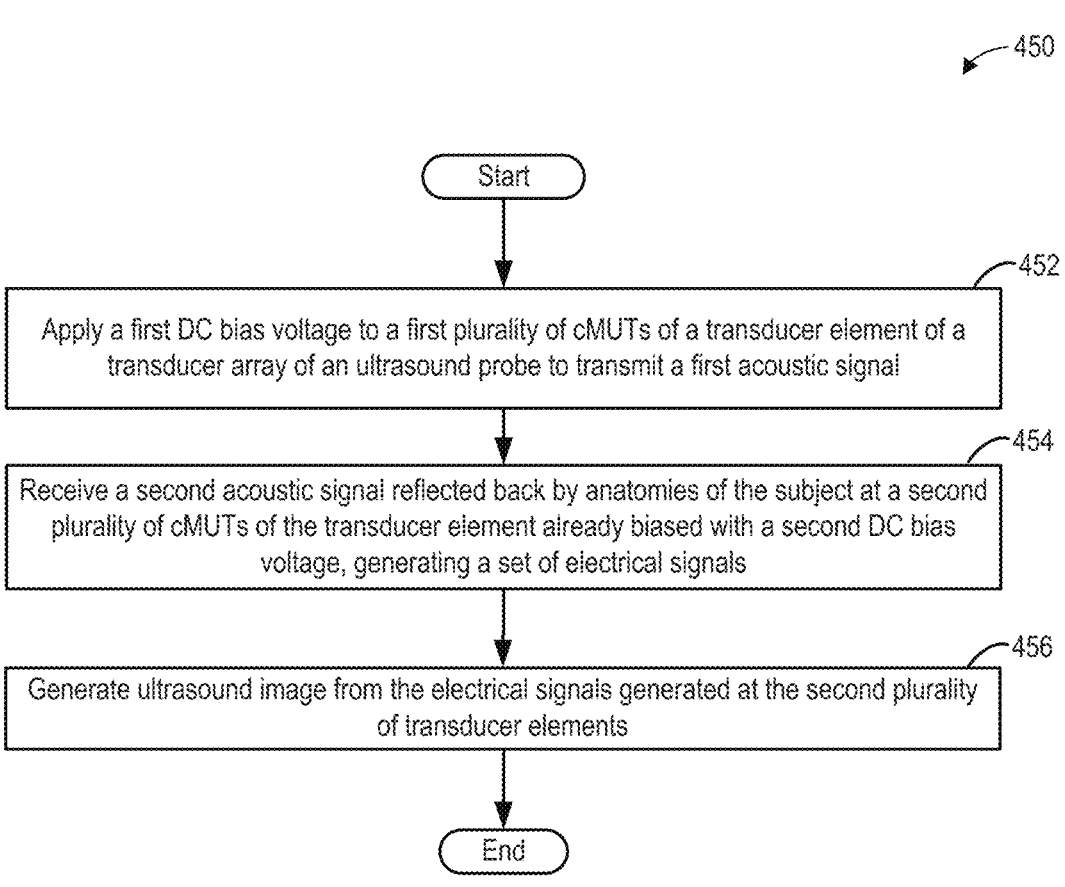

450

```
                    ┌──────────┐
                    │  Start   │
                    └──────────┘
                          │
                          ▼
┌────────────────────────────────────────────────────────────────┐  452
│  Apply a first DC bias voltage to a first plurality of cMUTs of a│
│  transducer element of a transducer array of an ultrasound probe │
│  to transmit a first acoustic signal                             │
└────────────────────────────────────────────────────────────────┘
                          │
                          ▼
┌────────────────────────────────────────────────────────────────┐  454
│  Receive a second acoustic signal reflected back by anatomies of │
│  the subject at a second plurality of cMUTs of the transducer    │
│  element already biased with a second DC bias voltage,           │
│  generating a set of electrical signals                          │
└────────────────────────────────────────────────────────────────┘
                          │
                          ▼
┌────────────────────────────────────────────────────────────────┐  456
│  Generate ultrasound image from the electrical signals generated │
│  at the second plurality of transducer elements                  │
└────────────────────────────────────────────────────────────────┘
                          │
                          ▼
                    ┌──────────┐
                    │   End    │
                    └──────────┘
```

FIG. 4B

HIGHER BANDWIDTH MICROMACHINED TRANSDUCERS MIXED WITH BIASING SCHEME

TECHNICAL FIELD

Embodiments of the subject matter disclosed herein relates to microelectromechanical systems (MEMS) devices and, in particular, micromachined ultrasonic transducers.

BACKGROUND

A microelectromechanical systems (MEMS) ultrasound device (hereafter, MEMS device) may be used for imaging and/or therapy targets such as organs and soft tissues in a human body, as well non-human targets. For example, the MEMS device may be used for applications such as ultrasound/acoustic sensing, non-destructive evaluation (NDE), ultrasound therapy (e.g., High Intensity Focused Ultrasound (HIFU)), etc., in addition to ultrasound imaging of humans, animals, etc. The MEMS device may rely on vibration of a membrane with a first electrode to receive and transmit signals.

MEMS devices may use real time, non-invasive high frequency (e.g., in a range of 100 KHz to tens of MHz) sound waves to produce a series of two-dimensional (2D) and/or three-dimensional (3D) images. The sound waves may be transmitted by a transmit transducer, and the reflections of the transmitted sound waves may be received by a receive transducer. The received sound waves may then be processed to display an image of the target. For some types of MEMS devices used as a transmit transducer and/or a receive transducer, such as a capacitive micromachined ultrasound transducer (cMUT), the cMUT may include a top electrode and a bottom electrode. The top electrode may move upon receiving electrical signals to generate sound waves or may move upon receiving sound waves to generate electrical signals that can be processed.

For cMUTs working mainly at higher frequencies, very thin membranes are desired to match a fractional bandwidth requirement of target applications. Although academic breakthroughs have been made with respect to manufacturing MUTs with sub-micron membrane thicknesses by surface micromachining, wafer bonding technologies, and parallel fabrication processes, industrial foundries working towards MUT industrialization in general suffer from a lack of sub-micron membrane capabilities. This shortcoming is closely related to a structural reliability of micro-electromechanical systems (MEMS) and wafer level device scalability targets of the sensors and actuator industry. Particularly for cMUTs, this constraint affects the device's bandwidth (e.g., fractional bandwidth) for higher frequency applications. As a result, methods for increasing the fractional bandwidth of cMUTs for high frequency applications without using sub-micron membranes would be desirable.

Approaches to the problem of increasing the fractional bandwidth of cMUTs for high frequency applications without decreasing membrane thickness include using a cMUT with a plurality of membranes. For example, U.S. Patent Application 20070059858A1 to Caronti teaches mixing different transducer elements and/or element geometries to address the bandwidth constraint. However, Caronti's cMUT suffers from a geometry related constraint, where a particular geometric configuration may be used to address a first target fractional bandwidth, a second geometrical configuration may be used to address a second target fractional bandwidth, a third geometrical configuration may be used to address a third target fractional bandwidth, and so on.

BRIEF DESCRIPTION

In one embodiment, a method for an ultrasound system comprises, during an ultrasound scan of a patient, and during a transmit mode of a transducer element of a transducer array of an ultrasound probe of the ultrasound system, applying a first DC bias voltage to a first portion of capacitive micromachined ultrasound transducers (cMUTs) of the transducer element; applying a second DC bias voltage to a second portion of cMUTs of the transducer element, the second DC bias voltage different from the first DC bias voltage; applying an AC drive signal to the first portion of cMUTs to generate a first acoustic signal based on a first combination of the first DC bias voltage and the AC drive signal, causing membranes of the first portion of cMUTs to vibrate at a first resonance frequency defined by the first DC bias voltage; applying the AC drive signal to the second portion of cMUTs to generate a second acoustic signal based on a second combination of the second DC bias voltage and the AC drive signal, the second combination causing membranes of the second portion of cMUTs to vibrate at a second resonance frequency defined by the second DC bias voltage, the second resonance frequency different from the first resonance frequency by a threshold difference; and combining the first acoustic signal and the second acoustic signal to generate a higher-bandwidth signal, the higher-bandwidth signal based on constructive interference between a first transmit transfer function of the first portion of cMUTs and a second transmit transfer function of the second portion of cMUTs. Similarly, during a receive mode of the transducer element, a higher-bandwidth input electrical signal may be generated, where the higher-bandwidth input electrical signal has a first component resulting from applying a first receive transfer function based on the first DC bias voltage to the first resonance frequency, and a second component resulting from applying a second receive transfer function based on the second DC bias voltage to the second resonance frequency, and the higher-bandwidth input electrical signal is based on constructive interference between the first receive transfer function and the second receive transfer function.

In contrast to approaches such as Caronti's, the method disclosed herein can be used with varied levels of frequency mixing, by applying the different DC bias voltages to electrodes of different cMUTs and hence inducing constructive coupling of different transmit and receive transfer functions used to generate an acoustic output signal from an electrical signal and generate an input electrical signal from a received acoustic wave. An advantage of the systems and methods disclosed herein is that a single ultrasound device may be configured for use by a plurality of applications that may demand different operating frequencies, including both lower and higher frequencies. The single ultrasound device would facilitate the use of the different applications, which would reduce a cost of the ultrasound system. Additionally, for higher frequency applications, unlike other alternative ultrasound devices that do not leverage interference between two resonances to produce a wider fractional bandwidth signal, the bandwidth of the ultrasound device described herein may not be constrained by a diameter of cMUTs included in the ultrasound device and/or a thickness of a membrane of the cMUTs. Further, the systems and methods disclosed herein may allow two or more adjacent cMUTs to be configured such that a first group of cMUT operates in collapsed operation mode, while a second group cMUT operates in non-collapse operation mode, where one of the first group and the second group is configured to transmit, and the other of the first group and the second group is configured to receive. In such a configuration the transmit and receive operation band may additionally be extended.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 4A shows an exemplary method for increasing a fractional bandwidth of an acoustic signal generated by a transducer array by introducing different bias voltages to different cMUTs of the transducer array, in accordance with one or more embodiments of the present disclosure.

FIG. 4B shows an exemplary method for applying different bias voltages to different cMUTs of the transducer array to convert a portion of the cMUTs into transmit cells, and a second portion of the cMUTs into receive cells, in accordance with one or more embodiments of the present disclosure;

DETAILED DESCRIPTION

Figure 1:
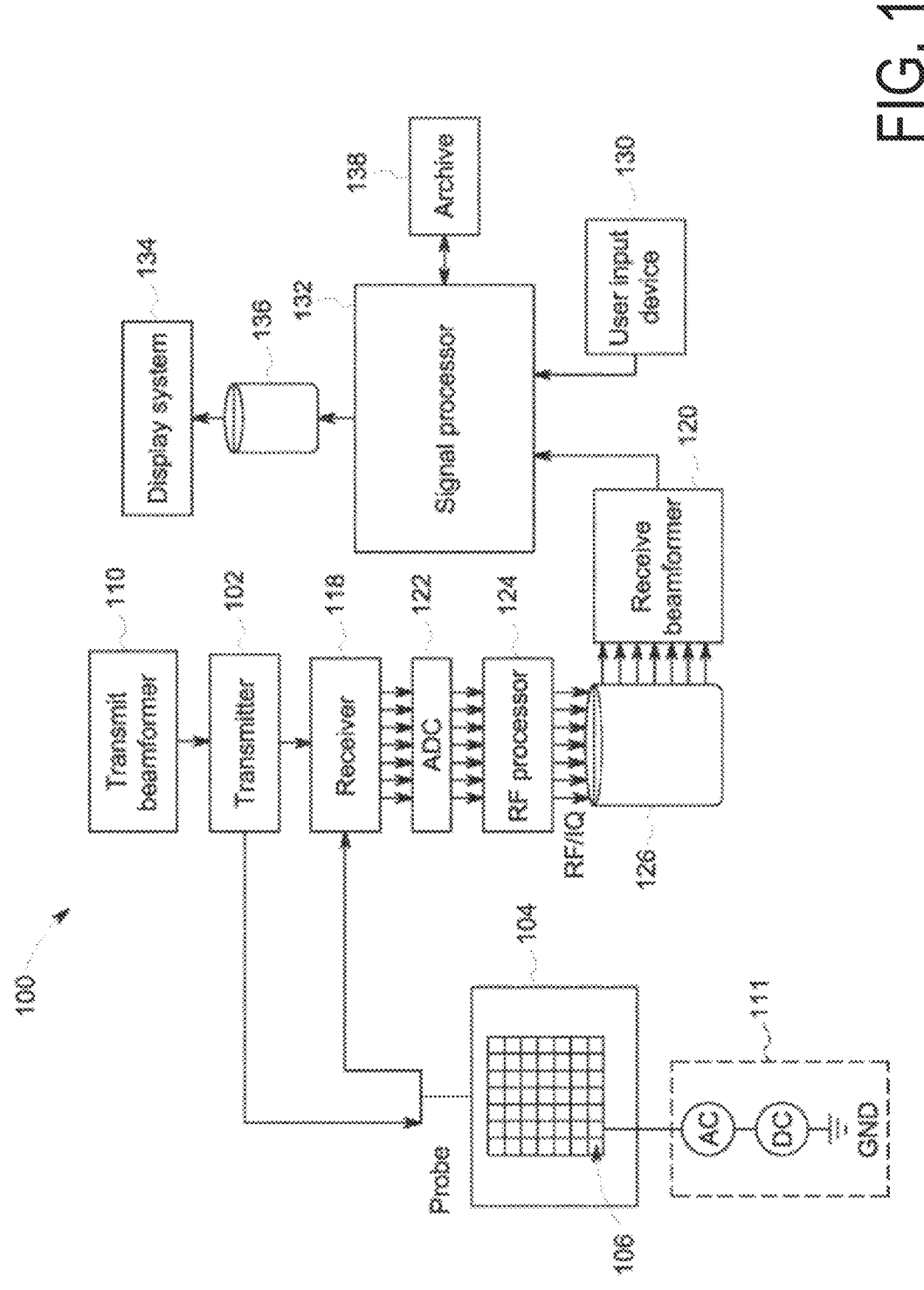
FIG. 1 shows a block diagram of an exemplary ultrasound system that may be used in ultrasound imaging, in accordance with one or more embodiments of the present disclosure.

An ultrasound system may include one or more detector arrays having a plurality of micromachined ultrasonic transducers (cMUTs). While a cMUT can be used for medical imaging, the cMUT may also be used for various other purposes such as, for example, ultrasound/acoustic sensing, non-destructive evaluation (NDE), ultrasound therapy (e.g., High Intensity Focused Ultrasound (HIFU)), etc., in addition to ultrasound imaging of humans or animals. The basic structure of a cMUT includes a thin membrane and a support substrate separated by a vacuum cavity. Typically, a doped silicon substrate makes up a bottom electrode of a capacitor and a conducting membrane acts as a top electrode. The membrane vibrates when excited with an electrical AC signal. Conversely, an electrical signal is generated when the membrane vibrates due to impinging sound waves.

cMUTs were originally fabricated using a sacrificial release process. In this process, a silicon nitride membrane layer is deposited on a patterned sacrificial polysilicon layer. The polysilicon is subsequently removed via small channels, and then a resulting gap is vacuum-sealed by a second silicon nitride layer deposited on top of the membrane. A final thickness of the membrane is established by etching back the second nitride layer. This technique has numerous intrinsic drawbacks, including stiction problems that may prevent the release of the membrane; stress in the membrane that is very sensitive to deposition conditions; difficulties in controlling the membrane thickness due to successive deposition and etching steps; and difficulties in controlling the gap height or thickness due to the unwanted non-uniform nitride deposition in the cavity during sealing.

More recently, cMUT fabrication processes have been developed utilizing a direct wafer bonding (e.g., fusion bonding) technique. In this technique, the vacuum cavities are formed by etching an oxide layer before the wafer is bonded to a silicon on-insulator (SOI) wafer in a vacuum chamber. After removing the handle wafer and the buried oxide (BOX) layer of the SOI wafer, a single crystal silicon layer remains as the cMUT membrane with good uniformity and without significant residual stress. However, for high frequency ultrasound devices, a thickness of the membrane may constrain a bandwidth of the electrical signal generated by the membrane.

To address this issue, a method is proposed whereby cMUTs of a transducer element are divided into a plurality of groups, and a different bias voltage is applied to each group of the plurality of groups to deliver different electrical signals to the cMUTs. As a result, the cMUTs may vibrate with different resonance frequencies. By leveraging constructive interference between the different resonance frequencies, a fractional bandwidth of the combined acoustic signals of the plurality of cMUTs may be increased, without relying on a thinner membrane.

The higher bandwidth may allow a single ultrasound device to be used for a greater number of higher and lower frequency applications. For the purposes of this disclosure, higher frequency applications comprise applications that rely on frequencies of between 20 and 50 MHz. For example, currently, a first ultrasound device may be used for a lower-frequency application (e.g., cardiac imaging); a second, different ultrasound device may be used for a higher-frequency application (e.g., tissue harmonic imaging) and a third ultrasound device may be used for a highest-frequency application (e.g., intravascular imaging). Using the mixed-bias strategy described herein, a single device may be configured for lower-frequency application, the higher-frequency application, and the highest-frequency application. By using the single device rather than the first, second, and third devices, a cost of the ultrasound system may be reduced, and an efficiency of a workflow of a radiologist may be increased.

Figure 2A:
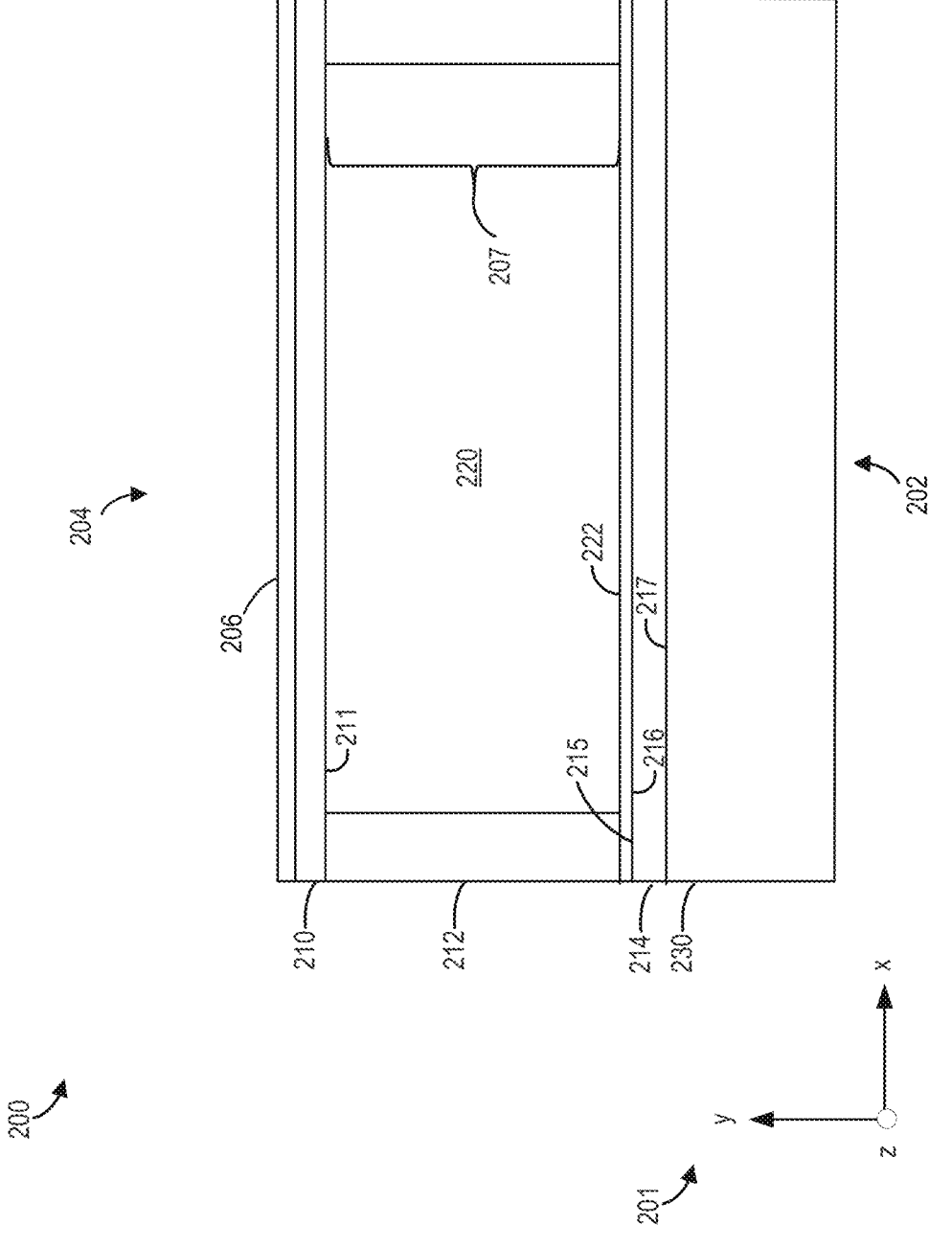
FIG. 2A shows an exemplary cross sectional view of a cMUT, as prior art.
Figure 5:
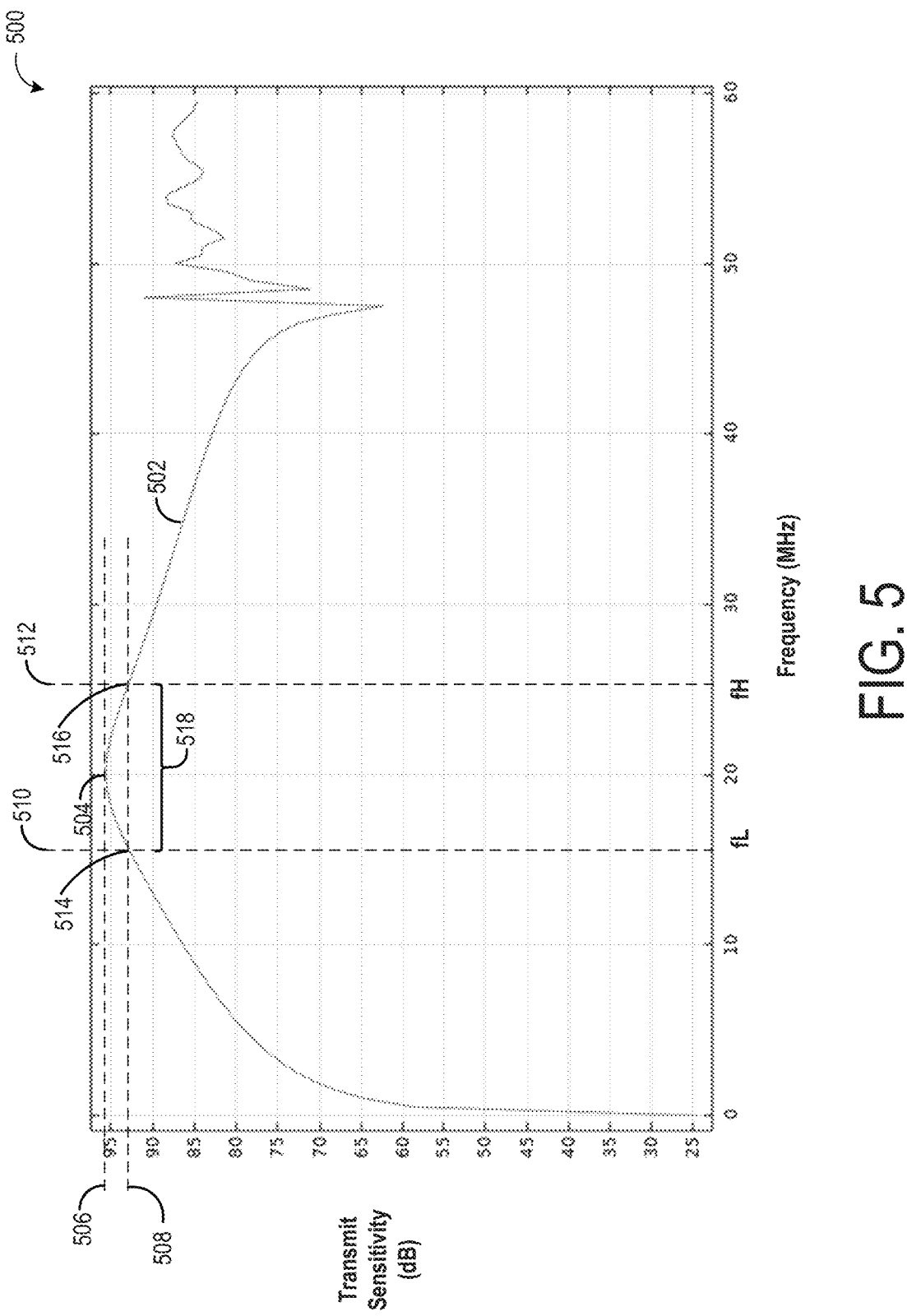
FIG. 5 shows a first transmit sensitivity graph indicating a first fractional bandwidth of an acoustic signal generated by a plurality of cMUTs, as prior art.
Figure 7:
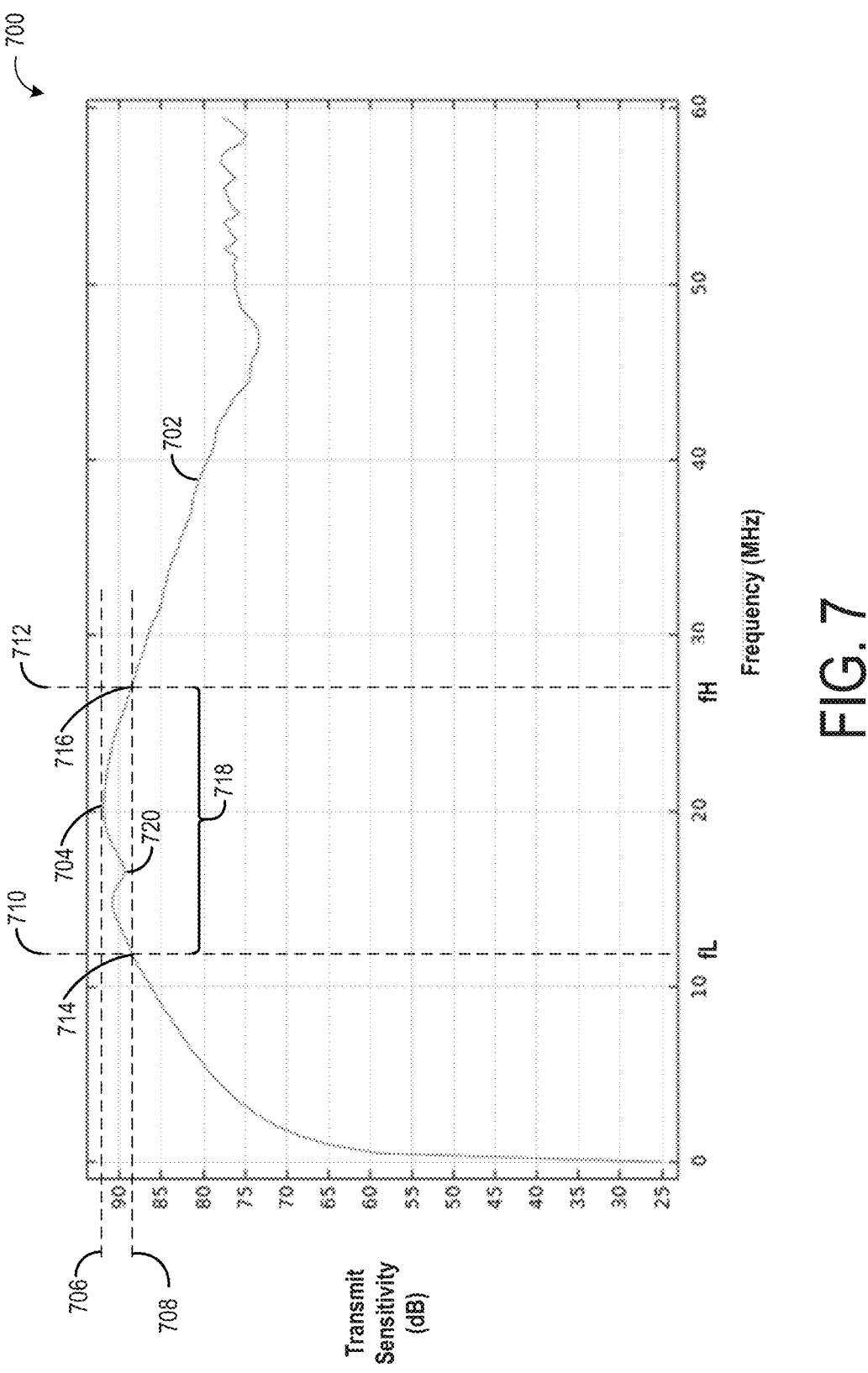
FIG. 7 shows a third transmit sensitivity graph indicating a third fractional bandwidth of an acoustic signal generated by a plurality of cMUTs, in accordance with one or more embodiments of the present disclosure.

FIG. 1 shows an exemplary ultrasound system. FIG. 2A shows an example of a cross section of a cMUT used in the ultrasound system of FIG. 1. A plurality of cMUTs may be arranged in a single transducer element array of the ultrasound system, such as the transducer array depicted in FIG. 2B. A one-dimensional (1D) transducer array may include a row of transducer elements, as shown in FIG. 3A. A two-dimensional (2D) transducer array may include a matrix of transducer elements, as shown in FIG. 3B. A first method for increasing a fractional bandwidth of a signal transmitted by the transducer array by vibrating different cMUTs of a transducer element at different resonance frequencies to leverage constructive interference is shown in FIG. 4A. A second method for converting a first portion of cMUTs of a transducer element into transmit cMUTs and a second portion of cMUTs of the transducer element into receive cMUTs is shown in FIG. 4B. FIG. 5 shows a first transmit sensitivity graph indicating a first fractional bandwidth of a first acoustic signal generated by a plurality of cMUTs, where a same electrical signal is generated at the plurality of cMUTs. In contrast, FIG. 7 shows a second transmit sensitivity graph indicating a second fractional bandwidth of a second acoustic signal generated by the plurality of cMUTs in a mixed-bias configuration where different electrical signals are generated at different groupings of cMUTs. In the mixed-bias configuration, transfer functions of different groupings may be damped by a coupling layer, to smooth sharp transitions during destructive interference. In various embodiments, the coupling layer may include rubber based polymers. An example of the coupling layer is shown in FIG. 3A.

Turning now to the figures, FIG. 1 is a block diagram of an exemplary ultrasound system 100 that may be used in ultrasound imaging, in accordance with various embodiments. The ultrasound system 100 comprises a transmitter 102, an ultrasound probe 104, a transmit beamformer 110, a receiver 118, a receive beamformer 120, A/D converters 122, an RF processor 124, an RF/IQ buffer 126, a user input device 130, a signal processor 132, an image buffer 136, a display system 134, and an archive 138. The circuit 111 is a non-limiting example of bias of a cMUT and variations in a configuration of the circuit 111 are possible without departing from the scope of the present disclosure.

The transmitter 102 may comprise suitable logic, circuitry, interfaces and/or code that may be operable to drive the ultrasound probe 104. The ultrasound probe 104 may comprise a group of transducer elements 106 that may each include, for example, a plurality of cMUTs. The cMUTs may comprise, for example, a single cMUT, a 1D array of cMUTs, 2D array of cMUTs, an annular (ring) array of cMUTs, etc. In certain embodiments, the ultrasound probe 104 may be operable to acquire ultrasound image data covering, for example, at least a substantial portion of an anatomy, such as the heart, a blood vessel, or any suitable anatomical structure. Each of the transducer elements 106 may be referred to as a channel.

The transmit beamformer 110 may comprise suitable logic, circuitry, interfaces and/or code that may be operable to control the transmitter 102 that drives the group of transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes can then be received by the transducer elements 106. For example, one or more drive circuits 111 may be coupled to and drive or control the electrodes of each transducer element 106. For example, the one or more drive circuits may be coupled to separate AC and DC voltage sources.

The group of transducer elements 106 in the ultrasound probe 104 may be operable to convert the received echoes into analog signals and communicated to a receiver 118. The receiver 118 may comprise suitable logic, circuitry, interfaces and/or code that may be operable to receive the signals from the ultrasound probe 104. The analog signals may be communicated to one or more of the plurality of A/D converters 122.

Accordingly, the ultrasound system 100 may multiplex such that ultrasonic transmit signals are transmitted during certain time periods and echoes of those ultrasonic signals are received during other time periods. Although not shown explicitly, various embodiments of the disclosure may allow concurrent transmission of ultrasonic signals and reception of echoes from those signals. In such cases, the probe may comprise transmit transducer elements and receive transducer elements.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF data, which may be, for example, I/Q signal data, real valued RF data, etc., may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

Accordingly, various embodiments may have, for example, the RF processor 124 process real valued RF data, or any other equivalent representation of the data, with an appropriate RF buffer 126. The receive beamformer 120 may comprise suitable logic, circuitry, interfaces and/or code that may be operable to perform digital beamforming processing to sum, for example, delayed, phase shifted, and/or weighted channel signals received from the RF processor 124 via the RF/IQ buffer 126 and output a beam summed signal. The delayed, phase shifted, and/or weighted channel data may be summed to form a scan line output from the receive beamformer 120, where the scan line may be, for example, complex valued or non-complex valued. The specific delay for a channel may be provided, for example, by the RF processor 124 or any other processor configured to perform the task. The delayed, phase shifted, and/or weighted channel data may be referred to as delay aligned channel data.

The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 may comprise a plurality of receive beamformers 120.

The user input device 130 may be utilized to input patient data, scan parameters, settings, select protocols and/or templates, and the like. In an exemplary embodiment, the user input device 130 may be operable to configure, manage, and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include switch(es), button(s), rotary encoder(s), a touchscreen, motion tracking, voice recognition, a mouse device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may comprise a touchscreen display.

The signal processor 132 may comprise suitable logic, circuitry, interfaces and/or code that may be operable to process ultrasound scan data (e.g., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in a live or off-line operation. In various embodiments, the processed image data can be presented at the display system 134 and/or stored at the archive 138. The archive 138 may be a local archive, a Picture Archiving and Communication System (PACS), or any suitable device for storing images and related information.

The signal processor 132 may comprise one or more central processing units, microprocessors, microcontrollers, and/or the like. The signal processor 132 may be an integrated component, or may be distributed across various locations, for example. In an exemplary embodiment, the signal processor 132 may be capable of receiving input information from the user input device 130 and/or the archive 138, generating an output displayable by the display system 134, and manipulating the output in response to input information from the user input device 130, among other things. The signal processor 132 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates may range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes worth of frames of ultrasound scan data. The frames of ultrasound scan data are stored in a manner to facilitate retrieval thereof according to its order or time of acquisition. The image buffer 136 may be embodied as any known data storage medium.

The display system 134 may be any device capable of communicating visual information to a user. For example, a display system 134 may include a liquid crystal display, a light emitting diode display, and/or any suitable display or displays. The display system 134 can be operable to present ultrasound images and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display. Additionally, while the ultrasound system 100 was described to comprise one receive beamformer 120, one RF processor 124, and one signal processor 132, various embodiments of the disclosure may use various number of processors. For example, various devices that execute code may be referred to generally as processors. Various embodiments may refer to each of these devices, including each of the RF processor 124 and the signal processor 132, as a processor. Furthermore, there may be other processors to additionally perform the tasks described as being performed by these devices, including the receive beamformer 120, the RF processor 124, and the signal processor 132, and all of these processors may be referred to as a "processor" for ease of description.

As described above, a probe for an imaging system, such as an ultrasound imaging system, or another type of medical system relying on data acquisition via acoustic signals, may incorporate cMUTs for transmitting and receiving signals. A performance of the cMUTs may rely on vibration of a membrane. For cMUTs working mainly at higher frequencies, very thin membranes are desired to match a fractional bandwidth requirement of target applications (e.g., submicron membrane thicknesses). While such very thin membranes may be obtained by surface micromachining, wafer bonding technologies, and/or parallel fabrication processes, due to a structural reliability of micro-electromechanical systems (MEMS) and wafer level device scalability targets of the sensors and actuator industry, industrial processes for generating sub-micron membrane thicknesses may be costly and inefficient.

FIG. 2A shows an exemplary embodiment of a cMUT 200, which may be included in a transducer element of an ultrasound system, such as one of transducer elements 106 of FIG. 1. A reference axis 201 is provided including a y-axis, an x-axis, and a z-axis.

In various embodiments, cMUT 200 may have a cylindrical shape, which in FIG. 2A has a bottom side 202 and a top side 204. In other embodiments, cMUT 200 may have a different shape. In one example, a radius of the cylindrical cMUT is 15 microns. It should be appreciated that the specific geometry used in this example is one configuration, and other embodiments cMUTs of different geometric configurations may be used without departing from the scope of this disclosure.

cMUT 200 includes a top electrode 206 at top side 204. A membrane layer 210 may be in face sharing contact and electrically coupled to top electrode 206. In some examples, membrane layer 210 may be formed of silicon. In one example, the membrane has a thickness of 2 microns. An insulating layer 212 may be in face sharing contact and with a bottom surface 211 of membrane layer 210. In some embodiments, insulating layer 212 or a similar insulation layer may be extend across bottom surface 211. In one example, insulating layer 212 has a thickness of 150 nm. A bottom electrode 214 at bottom side 202 may be in face sharing contact with a bottom surface 215 of insulating layer 212. In the depicted embodiment, insulating layer 212 comprises kerfs or side posts to support membrane layer 210. In some embodiments, an insulating layer 222 may extend across a top surface of bottom electrode 214. Further, in some embodiments, the kerfs may be constructed from a first material, and an insulating layer extending across the top surface of bottom electrode 214 may be constructed from a second material. In other words, the insulating layers 212 and/or 222 may be included either or both of above and below microcavity 220 and/or on one or both sides of microcavity 220.

Insulating layer 212 may not completely cover bottom surface 211 of membrane layer 210 and a top surface 216 of bottom electrode 214, thereby forming a microcavity 220 enclosed by membrane layer 210, insulating layer 212 and bottom electrode 214. Microcavity 220 may be evacuated or microcavity 220 may include an amount of fluid. In some examples, the fluid may be air. In one example, a height 207 of microcavity 220 (e.g., a gap between bottom surface 211 and top surface 216) is 75 nm. A bottom surface 217 of bottom electrode 214 may be in direct face sharing contact with a silicon substrate 230 (e.g., a wafer). Silicon substrate 230 may be an outermost layer when looking at cMUT 200 from bottom side 202. In some embodiments, silicon substrate 230 may comprise or act as a bottom electrode, and may be coupled to a common ground terminal.

cMUT 200 may be electrically coupled to a drive circuit that applies a combination of a DC bias signal and an AC drive signal via top electrode 206 and bottom electrode 214. The drive circuit may supply an AC drive signal voltage between first top electrode 206 and bottom electrode 214, which may cause a vibration of membrane layer 210. Specifically, the DC bias voltage fixes the instantaneous frequency of resonance and the AC drive voltage vibrates the membrane layer 210. The vibration of membrane layer 210 may in turn generate an acoustic wave that radiates away from a surface of top electrode 206, which may be directed towards an imaging target such as a body of a patient. In some cases, the DC bias voltage may be less than a threshold voltage (e.g., a collapse voltage) at which membrane layer 210 (and top electrode 206) collapses (e.g., operation in a non-collapse mode). The collapse voltage is the DC bias voltage at which bottom surface 211 of membrane layer 210 touches a top surface of insulation layer 222. In one example, the collapse voltage is 87.75 V. In other cases, the DC bias voltage may be equal to or greater than the collapse voltage (e.g., operation in a collapse mode).

The DC bias voltage is applied to top electrode 206 with bottom electrode 214 connected to a ground terminal of a cMUT. As described in greater detail below in reference to FIGS. 3-8, different DC bias voltages may be applied to different cMUTs of a transducer element to make the acoustic signal interfere in a way to generate a wider bandwidth output signal. Specifically, a first DC bias voltage may be applied to a first cMUT such that a first membrane layer of the first cMUT vibrates at a first resonance frequency, and a second DC bias voltage may be applied to a second cMUT such that a second membrane layer of the second cMUT vibrates at a second, different resonance frequency. In a transmit mode, when the AC drive signal is applied to the transducer element, the acoustic signal generated by the transducer element may have a wider bandwidth as a result of interference between a first transmit transfer function based on the first DC bias voltage and the AC drive signal, and a second transmit transfer function based on the second DC bias voltage and the AC drive signal.

Similarly, in a receive mode, when an acoustic signal is received at the transducer element, a first receive transfer function based on the first cMUT under the first DC bias voltage, and a second receive transfer function based on the second cMUT under the second DC bias voltage will interfere, generating a wider bandwidth output electrical signal.

In another embodiment, the first DC bias voltage may be greater than a collapse voltage applied to the first cMUT, and the second DC bias voltage may be less than the collapse voltage applied to the second cMUT. The first cMUT may be used for transmit mode, and the second cMUT may be used for a receive mode of the transducer element, or vice-versa.

Figure 2B:
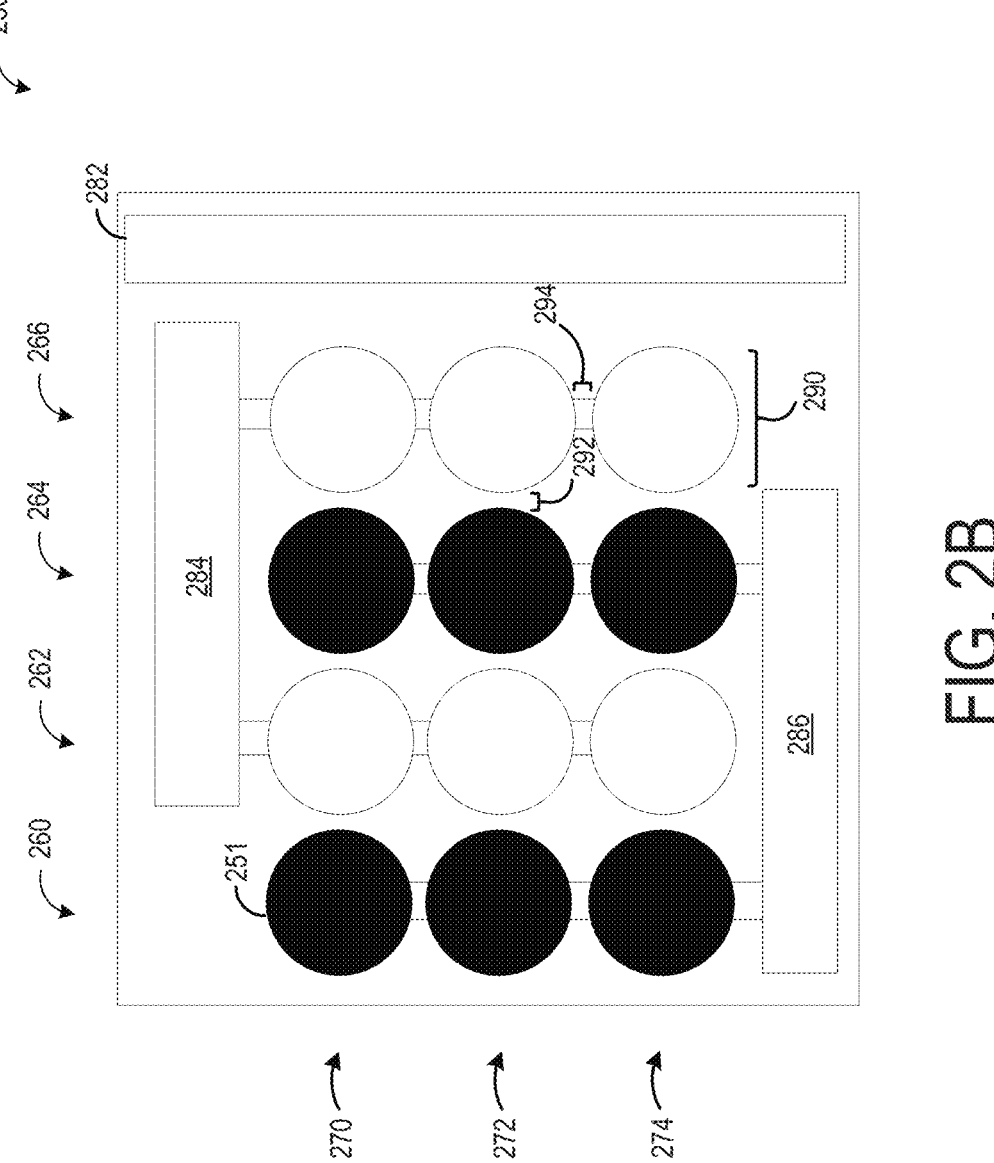
FIG. 2B shows a schematic representation of a single element transducer array of cMUTs, in accordance with one or more embodiments of the present disclosure.
Figure 3A:
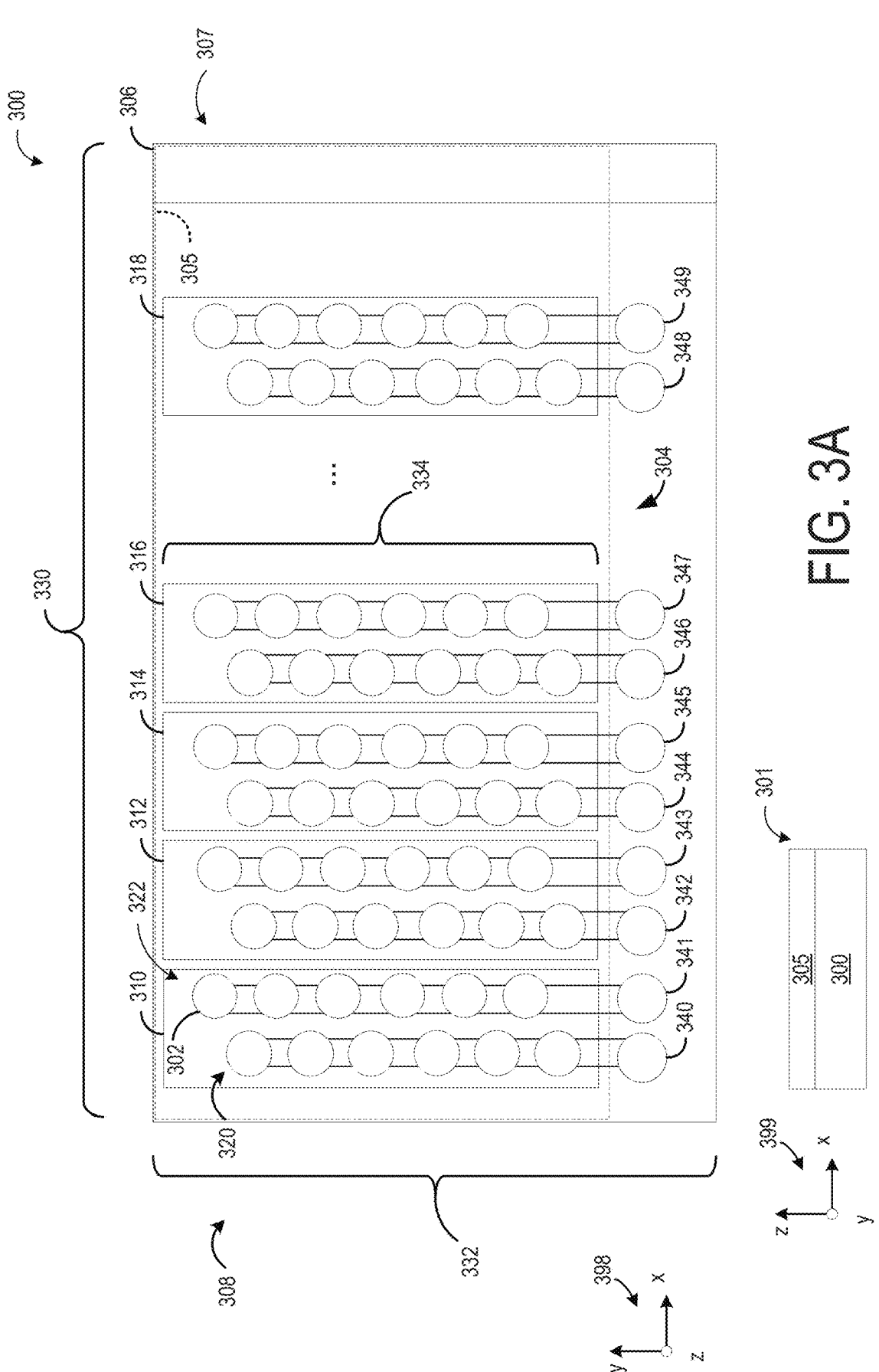
FIG. 3A shows a schematic representation of a one dimensional (1D) array of transducer elements, in accordance with one or more embodiments of the present disclosure.
Figure 3B:
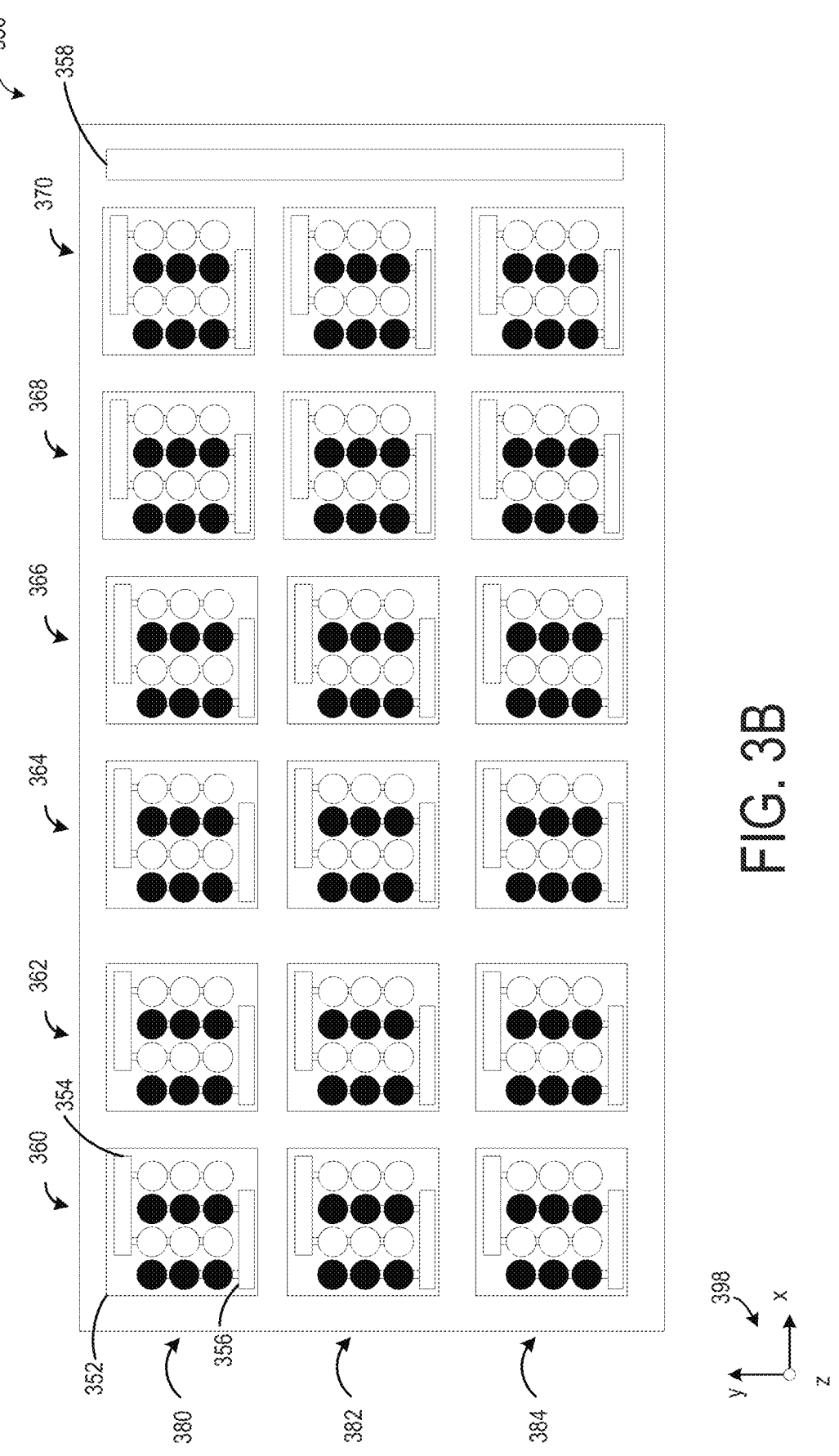
FIG. 3B shows a schematic representation of a two dimensional (2D) array of transducer elements, in accordance with one or more embodiments of the present disclosure.

A plurality of cMUTs may be arranged in a transducer element, as shown in FIG. 2B. In turn, a transducer array may comprise a plurality of transducer elements, which may be arranged in a row as shown in FIG. 3A, or in a 2D matrix, as shown in FIG. 3B.

FIG. 2B shows a single element transducer 250, where single element transducer 250 includes a plurality of cMUTs 251. In the depicted embodiment, the plurality of cMUTs 251 are arranged in a 4×3 matrix. The matrix includes a first column 260, a second column 262, a third column 264, and a fourth column 266; and a first row 270, a second row 272, and a third row 274. Each cMUT 251 may have a diameter 290, and each cMUT may be spaced apart from other adjacent cMUTs 251 by a horizontal distance (e.g., pitch) 292 and a vertical distance 294. Horizontal distance 292 may be the same as vertical distance 294, or horizontal distance 292 may be different from vertical distance 294. In one embodiment, diameter 290 is 30 microns, and the pitch is 5 microns.

Single element transducer 250 further includes a common ground terminal 282, which may ground electrical connections to the cMUTs 251, and a first common electrode 284 and a second common electrode 286 for providing a drive (AC) signal and bias (DC) signals to the cMUTs 251. Each of the plurality of cMUTs 251 may have a first electrode (e.g., top electrode 206 of FIG. 2A) electrically coupled to one of first common electrode 284 and second common electrode 286, and a second electrode (e.g., bottom electrode 214 of FIG. 2A) electrically coupled to common ground terminal 295. In the depicted embodiment, a first grouping of cMUTs in column 262 (depicted in white) and a second grouping of cMUTs in column 266 (depicted in white) are electrically coupled to first common electrode 284 and not coupled to second common electrode 286, and a third grouping of cMUTs in column 260 (depicted in black) and a fourth grouping of cMUTs in column 264 (depicted in black) are electrically coupled to second common electrode 286 and not coupled to first common electrode 284. Thus, the plurality of cMUTs may be divided into a first portion (depicted in white) energized by first common electrode 284, and a second portion (depicted in black) energized by second common electrode 286.

In a typical configuration of single element transducer 250, a voltage difference is generated at each cMUT 251, which causes a membrane (e.g., membrane layer 210) to resonate. Typically, the voltage difference is a combination of an AC voltage and a DC bias voltage applied at a single common electrode (not shown in FIG. 2B). In contrast, as shown in FIG. 2B, a different DC bias voltage may be provided to different cMUTs 251 of single element transducer 250 at common electrodes 284 and 286. In other words, a first DC bias voltage may be applied to the cMUTs of columns 260 and 264 via first common electrode 284, and a second DC bias voltage may be applied to the cMUTs of columns 262 and 266 via second common electrode 286. In other embodiments, additional, different bias voltages may be applied to different groupings of cMUTs, for example, in different columns of single element transducer 250. By applying the different DC voltages to the different cMUTs, the different cMUTs may resonate at different frequencies. The difference in frequencies between the different cMUTs may be exploited to increase a fractional bandwidth of an acoustic signal generated by single element transducer 250.

Additionally or alternatively, different DC bias voltages may be applied to different groups of cMUTs 251 of single element transducer 250 to configure a first set of cMUTs as receive cells, and a second set of cMUTs as transmit cells.

Referring to FIG. 3A, an exemplary 1D transducer array 300 of an ultrasound system such as ultrasound system 100 is shown. Transducer array 300 includes a 1D array of transducer elements with a width 330 and a height or elevation 332, where the transducer elements may be similar to single element transducer 250 of FIG. 2B. Transducer array 300 includes a plurality of transducer elements 304 aligned in a row, including transducer elements 310, 312, 314, 316, and 318. Each transducer element 304 has an elevation 334. In other embodiments, transducer elements 304 may be arranged in different configurations. For example, in other embodiments, transducer array 300 may include a different total number of transducer elements 304, and/or columns of transducer array 300 may each include a different number of transducer elements 304 (e.g., in various configurations).

Each transducer element 304 may include a plurality of cMUTs 302, which may be non-limiting examples of cMUT 200 of FIG. 2A. Each cMUT 302 may generate an acoustic signal based on a vibration of a membrane of the cMUT, as described above. Each cMUT 302 may be positioned within each transducer element 304 with a spacing. For example, the spacing may be 5 microns.

Additionally, isolation may be provided between transmit and receive circuitry of transducer array 300 to protect the receive circuitry from the high voltages used during transmit. In systems using a shared transmit driver, the low voltage connections (e.g., receive signal paths) may be temporarily connected to a common ground terminal 306 at a first side 307 to protect the channels from high potentials, while a second side 308 of transducer array 300 that is normally a shared ground during receive is pulsed with a high voltage to generate a plane wave output from all of the cMUTs 302. This type of isolation has typically been provided via multiplexer switches to ground or disconnecting the receive circuitry from the transducer elements during transmission.

In a typical transducer array of an ultrasound system, an electrical signal may be applied to each cMUT 302 to induce a voltage difference between a top electrode of a respective cMUT 302 and a bottom electrode of the respective cMUT 302, as described above in reference to top electrode 206 and bottom electrode 214 of cMUT 200 of FIG. 2A. The electrical signal may be a combination of an AC signal and a DC bias signal. The voltage difference generates an acoustic wave via a first vibration of a membrane layer (e.g., membrane layer 210), which may be directed at an anatomy of a patient. The acoustic wave may be reflected back by portions of the anatomy, and may be received at the respective cMUT (or a different cMUT). The received acoustic wave may cause a second vibration of the membrane layer. The second vibration may be converted into an acoustic signal. The acoustic signals of the cMUTs are converted to an electrical signal.

However, as described in greater detail below in reference to FIG. 4A, different vibrations may be induced at different cMUTs 302 by applying different electrical signals to the different cMUTs 302. The different electrical signals may be generated by applying different bias voltages to different cMUTs 302. In other words, the cMUTs 302 of a transducer element 304 may be divided into different groupings that are electrically connected to different bias voltage pads (e.g., electrodes), such that each grouping may be assigned a different bias voltage.

For example, in the depicted embodiment, a first bias voltage may be applied to a first grouping 320 of cMUTs 302 of transducer element 310 via a first bias voltage pad 340, and a second bias voltage may be applied to a second grouping 322 of cMUTs 302 of transducer element 310 via a second bias voltage pad 341. Similarly, a third bias voltage may be applied to a first grouping of cMUTs 302 of transducer element 312 via a third bias voltage pad 342, and a fourth bias voltage may be applied to a second grouping of cMUTs 302 of transducer element 312 via a fourth bias voltage pad 343. In some embodiments, two different bias voltages may be used, where the third bias voltage may be equal to the first bias voltage, and the fourth bias voltage may be equal to the second bias voltage. In other embodiments, any or all of the first, second, third, and fourth bias voltages may be different. Similar bias voltage pads 344, 345, 346, 347, 348, and 349 may be used to apply equal or different bias voltages to associated groups of cMUTs 302 of transducer elements 314, 316, and 318.

In case of SOI based bonding technology where cell level electrical insulation would be required for bias driven frequency mixing between two cMUTs, an already inherent etch-based element seclusion procedure can be used to connect alternate or adjacent cMUTs to one of first bias voltage pad 324 and second bias voltage pad 326. In some embodiments, such as in advanced 2D arrays, the cMUTs connections may be bundled through a back side of the wafer (e.g. silicon substrate 230) with through-wafer via connections.

With respect to transducer element 310, and accordingly for other transducer elements of transducer array 300, membranes of cMUTs 302 of first grouping 320 may resonate at a first resonance, and membranes of cMUTs 302 of second grouping 322 may resonate at a second resonance. The first and second resonances may be converted into acoustic signals and combined, leveraging interference to produce a wider bandwidth acoustic signal through constructive coupling.

Transducer array 300 is depicted in x and y dimensions, as indicated by reference axes 398. FIG. 3A includes a cross-sectional perspective 301 of transducer array 300, in which transducer array is depicted in x and z dimensions. In various embodiments, as shown in cross-sectional perspective 301, a coupling layer 305 may cover a surface of transducer array 300, which may be used to dampen sharp frequency transitions in a transfer function generated from destructive interference of two different transmit transfer functions originating from the two DC bias voltages, as described in greater detail below in reference to FIGS. 6 and 7. For examples such as FIG. 3A, where electrical connections are not formed through a back side of the wafer via through-wafer via technologies, coupling layer 305 may cover regions of transducer array 300 including transducer elements 302 and a portion of common ground terminal 306, but not including voltage bias pads 340-349, as indicated by a dashed box in FIG. 3A.

Coupling layer 305 may be constructed from soft solids (e.g., rubber and/or polymers), which may reduce a destructive interference between different groupings of cMUTs caused by membranes of the cMUTs of the different groupings resonating at different resonance frequencies, due to receiving different bias voltages. For example, first grouping 320 may resonate at a first resonance frequency as a result of receiving the first bias voltage via first bias voltage pad 340, and second grouping 322 may resonate at a second resonance frequency as a result of receiving the second bias voltage via second bias voltage pad 341. By including coupling layer 305, a destructive interference between a first transmit transfer function of first grouping 320, and a second transmit transfer function of second grouping 322 may be reduced, as described in greater detail below in reference to FIGS. 7 and 8.

Referring now to FIG. 3B, a 2D transducer array 350 is shown, where 2D transducer array 350 includes a plurality of transducer elements 352 arranged in a matrix. In the depicted embodiment, the matrix has six columns, including a first column 360, a second column 362, a third column 364, a fourth column 366, a fifth column 368, and a sixth column 370. The matrix has three rows, including a first row 380, a second row 382, and a third row 384. As described in reference to FIG. 3A, each transducer element 352 of 2D transducer array 350 may include various bias voltage pads or electrodes capable of delivering different bias voltages to different groups of cMUTs within the transducer element 352. For example, each transducer element 352 may include a first electrode 354 and a second electrode 356, where a first bias voltage may be applied to a first portion of cMUTs (depicted in white) of a respective transducer element 352 via first electrode 354, and a second bias voltage may be applied to a second portion of cMUTs (depicted in black) of a respective transducer element 352 via second electrode 356. All of the cMUTs of each transducer element may be electrically coupled to a common ground terminal 358 (e.g., common ground terminal 282 of FIG. 2B). In this way, membranes of different groups of cMUTs within various transducer elements 352 may be caused to resonate at different frequencies, as described above. For embodiments of 2D arrays such as 2D transducer array 350, all electrical connections may be made via through-wafer via technologies through a back side of the wafer as is well known in the art.

FIG. 4A shows an exemplary method 400 for increasing a fractional bandwidth of an acoustic signal generated from a plurality of cMUTs of an ultrasound system, such as ultrasound system 100 of FIG. 1. The cMUTs may be non-limiting examples of cMUT 200 of FIG. 2A, and the cMUTs may be arranged within transducer elements of a transducer array in a configuration similar to transducer array 300 of FIG. 3A and/or 2D transducer array 350 of FIG. 3B. To increase the bandwidth, a first set of acoustic signals generated by a first grouping of cMUTs within a transducer element (e.g., first grouping 320 of transducer element 310) may be combined with a second set of acoustic signals generated by a second grouping of cMUTs within the same transducer element. The first set of acoustic signals are generated from membranes of the first set of cMUTs vibrating at a first resonance frequency, and the second set of acoustic signals are generated from membranes of the second set of cMUTs vibrating at a second resonance frequency. Method 400 may be executed by a signal processor of an ultrasound system, such as signal processor 132 of ultrasound system 100 of FIG. 1. Method 400 may be performed during a scan of a patient using the ultrasound system.

At 402, the method includes applying a first DC bias voltage to a first grouping of cMUTs (e.g., first grouping 320) of a transducer element of a transducer array. The transducer array may include a plurality of transducer elements, which may be configured as a 1D transducer array as in FIG. 3A, a 2D transducer array as in FIG. 3B, or a different configuration. The first bias voltage may be applied via a first bias voltage pad of the transducer element, such as first bias voltage pad 324 of FIG. 3A.

At 404, the method includes applying a second DC bias voltage to a second grouping of cMUTs (e.g., second grouping 322) of the transducer element, where the second bias voltage is different from the first bias voltage (e.g., where a difference between the second bias voltage and the first bias voltage is greater than a threshold voltage). The second bias voltage may be applied via a second bias voltage pad of the transducer element, such as second bias voltage pad 326 of FIG. 3A. As described in greater detail below in reference to FIG. 6, the first bias voltage and the second bias voltage may be selected in a way such that the destructive interference coming from the two output signals can be damped substantially by the coupling layer (e.g., coupling layer 305 of FIG. 3A).

For example, in some embodiments, the cMUTs included in each transducer element of the transducer array may be divided into two groupings. The first bias voltage may be applied to a first grouping of cMUTs of a first transducer element, a first grouping of cMUTs of a second transducer element, a first grouping of cMUTs of a third transducer element, and so on. The second bias voltage may be applied to a second grouping of cMUTs of a first transducer element, a second grouping of cMUTs of a second transducer element, a second grouping of cMUTs of a third transducer element, and so on. It should be appreciated that while method 400 is described with respect to two groupings of cMUTs of each transducer element, in other embodiments, a greater number of bias voltages may be applied to a respective greater number of groupings of cMUTs. For example, a third bias voltage may be applied to a third grouping of cMUTs of the transducer element; a fourth bias voltage may be applied to a fourth grouping of cMUTs of the transducer element; and so on. Further, in some embodiments, different bias voltages may be applied to different cMUTs at different transducer elements. For example, the first and second bias voltages may be applied to different groupings of a first transducer element; the third and fourth bias voltages may be applied to different groupings of a second transducer element; a fifth and a sixth bias voltage may be applied to different groupings of a third transducer element; and so on.

Returning to the example of two DC bias voltages, in response to the first bias voltage, membranes of the first grouping of cMUTs may resonate at a first resonance. The first DC bias voltage may be applied at an electrode of each cMUT of the first grouping of cMUTs, such that respective membranes of the first grouping may vibrate at a first resonance frequency in response to an applied AC drive signal. Similarly, the second DC bias voltage may be applied at an electrode of each cMUT of the second grouping of cMUTs, such that respective membranes of the second grouping may vibrate at a second resonance frequency in response to the same applied AC drive signal (where a difference between the second resonance frequency and the first resonance frequency is greater than a threshold difference). The electrodes may be a top electrode (e.g., top electrode 206) of the cMUT, or a bottom electrode (e.g., bottom electrode 214) of the cMUT.

A resonant frequency of a micromachined membrane may be determined by equation 1 below:

$$f_0 = \frac{1}{2\pi}\sqrt{\frac{k}{m}} \tag{1}$$

where k represents an inherent spring constant, and m is a mass of the membrane. As can be seen, the resonant frequency of the membrane varies directly with the spring constant and inversely with the mass. Assuming a small signal model of a cMUT, whose ideal structure includes a clamped membrane, a DC bias voltage may be applied to an electrode (e.g., top electrode 206 or bottom electrode 214 of FIG. 2A) of the cMUT to generate a spring softening effect, which reduces an effective stiffness of the resonant frequency of the membrane by a factor, described below in equation 2:

$$k_{soft} = \frac{\varepsilon_0 A V_{DC}^2}{g_{eff}^3} \tag{2}$$

where, $\varepsilon_0$, A, $V_{DC}$, and $g_{eff}$ are the dielectric constant of free space, coupling area of the electrode, applied DC bias voltage, and effective gap height of the cMUT device, respectively. The effective gap height in relation to the vacuum/air gap height (go) and the insulation layer (thickness ($t_i$) and dielectric constant ($\varepsilon$)) can be expressed as:

$$g_{eff} = g_0 + \frac{t_i}{\varepsilon} \tag{3}$$

Thus, the resonant frequency of the cMUT membrane in relation to the changed spring constant and hence the DC bias voltage can be expressed as:

$$f_{ss} = \frac{1}{2\pi}\sqrt{\frac{k - k_{soft}}{m}} \tag{4}$$

By applying a first DC bias voltage to the first electrode of the first transducer element, and applying a second, different DC bias voltage to the second electrode of the second transducer element, the spring softening effect for the first membrane may be different from the spring softening effect for the second membrane. As a result, the first membrane may have a first resonant frequency, and the second membrane may have a second, different resonant frequency.

At 406, method 400 includes generating a higher-bandwidth acoustic signal as a result of applying an AC drive voltage to both of the first plurality of cMUTs and the second plurality of cMUTs. When the AC drive voltage is applied to the first plurality of cMUTs, a first electrical signal is generated based on the AC drive voltage and the first DC bias voltage. When the AC drive voltage is applied to the second plurality of cMUTs, a second, different electrical signal is generated based on the AC drive voltage and the second DC bias voltage. As the frequency response of the two devices based on the first electrical signal and the second electrical signal are different, they result in two different transmit transfer functions. Interference between a first transmit transfer function and a second transmit transfer function of the two different transmit transfer functions may thus be exploited to generate the higher-bandwidth signal.

At 408, the method includes receiving a reflected acoustic wave reflected back by the anatomies of the subject at the plurality of transducer elements, and generating an ultrasound image. When the transducer elements operate in the receive mode, the first plurality of cMUTs are already biased with the first DC bias voltage, and the second plurality of cMUTs are already biased with the second DC bias voltage. As a result, membranes of the first plurality of cMUTs may resonate at the first resonance frequency, and membranes of the second plurality of cMUTs may resonate at the second resonance frequency. A first receive transfer function generated at the first plurality of cMUTs by the acoustic signal and a second receive transfer function generated at the second plurality of cMUTs by the acoustic signal may interfere, generating an electrical output signal with a wider fractional bandwidth than an alternative fractional bandwidth that may be obtained if the first DC bias voltage is equal to the second DC bias voltage. In this way, the benefit in terms of the increased fractional bandwidth is obtained both for the transmit and receive cases.

FIG. 4B shows an exemplary method 450 for advantageously applying different DC bias voltages to different portions of cMUTs of one or more transducer elements within a transducer array of an ultrasound system, such as ultrasound system 100 of FIG. 1, to configure a first portion of the cMUTs to transmit a first acoustic signal, and configure a second, different portion of the cMUTs to receive a second acoustic signal reflected back from anatomies of a patient. The cMUTs may be non-limiting examples of cMUT 200 of FIG. 2A, and the cMUTs may be arranged within transducer elements of a transducer array in a configuration similar to transducer array 300 of FIG. 3A and/or 2D transducer array 350 of FIG. 3B. The first acoustic signal is generated from membranes of the first portion of cMUTs vibrating at a first resonance frequency. The second acoustic signal causes membranes of the second portion of cMUTs to vibrate at a second resonance frequency, generating electrical signals that may be combined to generate an image.

Method 450 may be executed by a signal processor of an ultrasound system, such as signal processor 132 of ultrasound system 100 of FIG. 1. Method 400 may be performed during a scan of a patient using the ultrasound system.

At 452, the method includes applying a first DC bias voltage to a first plurality of cMUTs (e.g., first grouping 320) of a transducer element of a transducer array. The same DC bias voltage may be applied to each cMUT of the first plurality of cMUTs. The transducer array may include a plurality of transducer elements, which may be configured as a 1D transducer array as in FIG. 3A, a 2D transducer array as in FIG. 3B, or a different configuration. The first DC bias voltage may be applied via a first bias voltage pad of the transducer element, such as first bias voltage pad 340 of FIG. 3A. The first bias voltage may be more than a collapse voltage of the cMUTs, or less than a collapse voltage (e.g., a non-collapse voltage) of the cMUTs. When the first set of electrical signals are applied to the first plurality of cMUTs, membranes of the first plurality of cMUTs may resonate at a first resonance frequency, generating a first acoustic signal. The first acoustic signal may be directed towards anatomies of the patient during the scan.

At 454, the method includes receiving a second acoustic signal reflected back from anatomies of the patient at a second plurality of cMUTs, where the second plurality of cMUTs includes different cMUTs than the first plurality of cMUTs. When the second acoustic signal is received at the second plurality of cMUTs, the second plurality of cMUTs may be already biased with a second, different DC bias voltage, such that membranes of the second plurality of cMUTs may resonate at a second, different resonance frequency, generating a set of electrical signals at electrodes of the cMUTs, as described above. The second bias voltage may be applied via a second bias voltage pad of the transducer element, such as second bias voltage pad 341 of FIG. 3A. The second bias voltage may be greater than a collapse voltage of the cMUTs, or less than the collapse voltage of the cMUTs. In other words, if the first bias voltage of the first plurality of cMUTs is greater than the collapse voltage, then the second bias voltage of the second plurality of cMUTs may be less than the collapse voltage, and if the first bias voltage of the first plurality of cMUTs is less the collapse voltage, then the second bias voltage of the second plurality of cMUTs may be greater than the collapse voltage. In this way, the different DC bias voltages may be advantageously used to configure different cMUTs of a single transducer element to act as receive cMUTs or transmit cMUTs.

At 456, the method includes generating an ultrasound image of the anatomies of the subject based on the electrical signals generated by the second plurality of cMUTs at each transducer element of the transducer array, and method 400 ends.

FIG. 5 shows a first transmit sensitivity graph 500 of a combined acoustic signal 502 generated by a plurality of cMUTs of a transducer array, such as transducer array 300 of FIG. 3A, when a single AC drive voltage is applied to the plurality of cMUTs configured with a same DC bias voltage. In the embodiment depicted in first transmit sensitivity graph 500, a homogenous DC bias voltage of 80% of a collapse voltage of the cMUTs is applied to the plurality of cMUT cells. For example, the collapse voltage may be 87.75 V. First transmit sensitivity graph 500 shows a variance in an output pressure of the plurality of cMUT cells as a function of frequency, at 80% of the collapse voltage, under liquid loading conditions. The cMUTs may be non-limiting examples of cMUT 200 of FIG. 2A. Transmit sensitivity is shown on the y axis of first transmit sensitivity graph 500, and a resulting frequency is shown on the x axis.

Acoustic signal 502 peaks at a point 504, corresponding to a maximum sensitivity of roughly 96 dB, as indicated by dashed line 506. A second dashed line 508 indicates a 3 dB decrease in sensitivity from the maximum sensitivity indicated by point 504. Thus, a fractional bandwidth 518 of acoustic signal 502 may be defined as a range of frequencies within which the output sensitivity is 3 dB less than the peak sensitivity at point 504). Fractional bandwidth 518 may be calculated by measuring a frequency range between a lowest frequency (fL) indicated by a first point 514 where dashed line 508 intersects with acoustic signal 502, and a highest frequency (fH) indicated by a second point 516 where dashed line 508 intersects with acoustic signal 502. Fractional bandwidth 518 may be calculated according to the following formula:

$$2 * \left[ (fH - fL)/(fH + fL) \right] \times 100 \qquad (1)$$

In first transmit sensitivity graph 500, fL is 15.5 MHz, as indicated by a dashed line 510, and fH is 26 MHz, as indicated by a dashed line 512, and fractional bandwidth 518 is 51.47%. A central resonance frequency of the plurality of cMUTs at 80% of the collapse value under the liquid loading conditions is approximately 20 MHz, as indicated by the peak at point 504.

Figure 6:
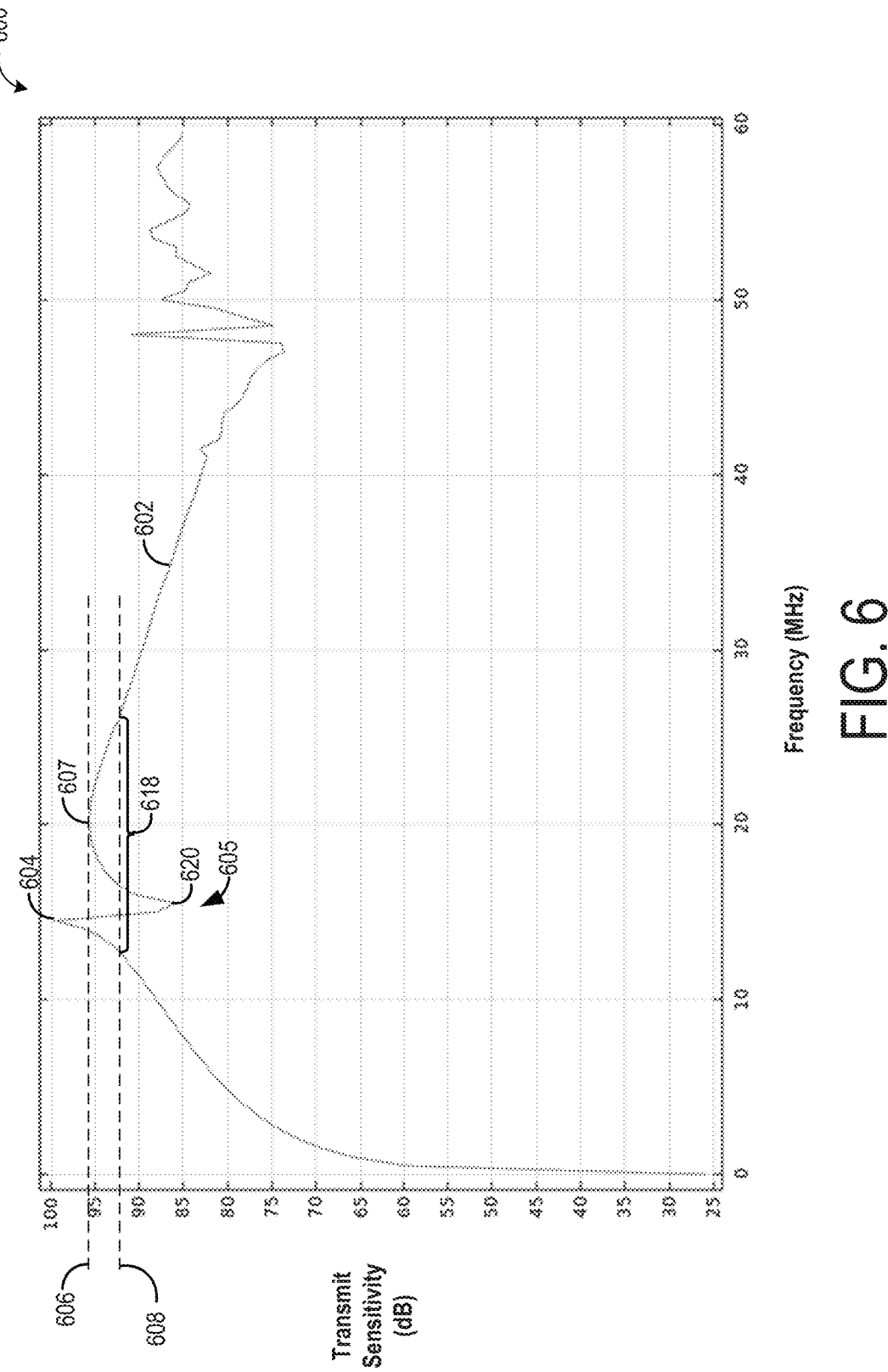
FIG. 6 shows a second transmit sensitivity graph indicating a second fractional bandwidth of an acoustic signal generated by a plurality of cMUTs, in accordance with one or more embodiments of the present disclosure.

FIG. 6 shows a second transmit sensitivity graph 600 of a combined acoustic signal 602 generated by the plurality of cMUTs of FIG. 5, but with a mixed-bias configuration, where different DC bias voltages are applied to different cMUTs of the plurality of cMUTs. In other words, the plurality of cMUTs are divided into two portions, which may each include a similar number of cMUTs (e.g., first grouping 320 and second grouping 322 of FIG. 3A). In the depicted embodiment, a bias voltage of 90% of the collapse voltage is applied to a first portion of the plurality of cMUTs, and a bias voltage of 70% of the collapse voltage is applied to a second portion of the plurality of cMUTs. In other embodiments, different percentages of the collapse voltage may be applied to the first and second portions of the plurality of cMUTs, provided that they are different (e.g., where a difference between the bias voltages is greater than a threshold voltage.

A notch 605 is shown between 10 MHz and 20 MHz, where a frequency transition occurs. The frequency transition is a sharp transition, where acoustic signal 602 rises to a peak 604, subsequently descends to a trough 620, and then rises again to a second peak 607, within a short difference in frequencies around 15-16 MHz. Notch 605 is caused by a destructive interference between a first transmit transfer function applied to the first portion of the plurality of cMUTs, and a second transmit transfer function applied to the second portion of the plurality of cMUTs. Mechanically, this can be seen as the first portion and the second portion of the cMUTs vibrating 180 degrees out of phase, as described below in reference to FIG. 8. As a result of the destructive interference, when a fractional bandwidth 618 is calculated based on a 3 dB decrease in amplitude from peak 607, as indicated by dashed lines 606 and 608, a depth of notch 605 intervenes in the 3 dB calculation path, thereby reducing fL substantially. As a result, the fractional bandwidth may be reduced to a lower level than fractional bandwidth 518 of FIG. 5. To mitigate the destructive interference and dampen the notch to smooth a combined transmit transfer function including the first transfer function and the second transfer function and/or smooth the frequency band of interest, a coupling layer (e.g., coupling layer 305 of FIG. 3A) may be included that covers both the first portion of the plurality of cMUTs and the second portion of the plurality of cMUTs, as described above in reference to FIG. 3A.

Figure 8:
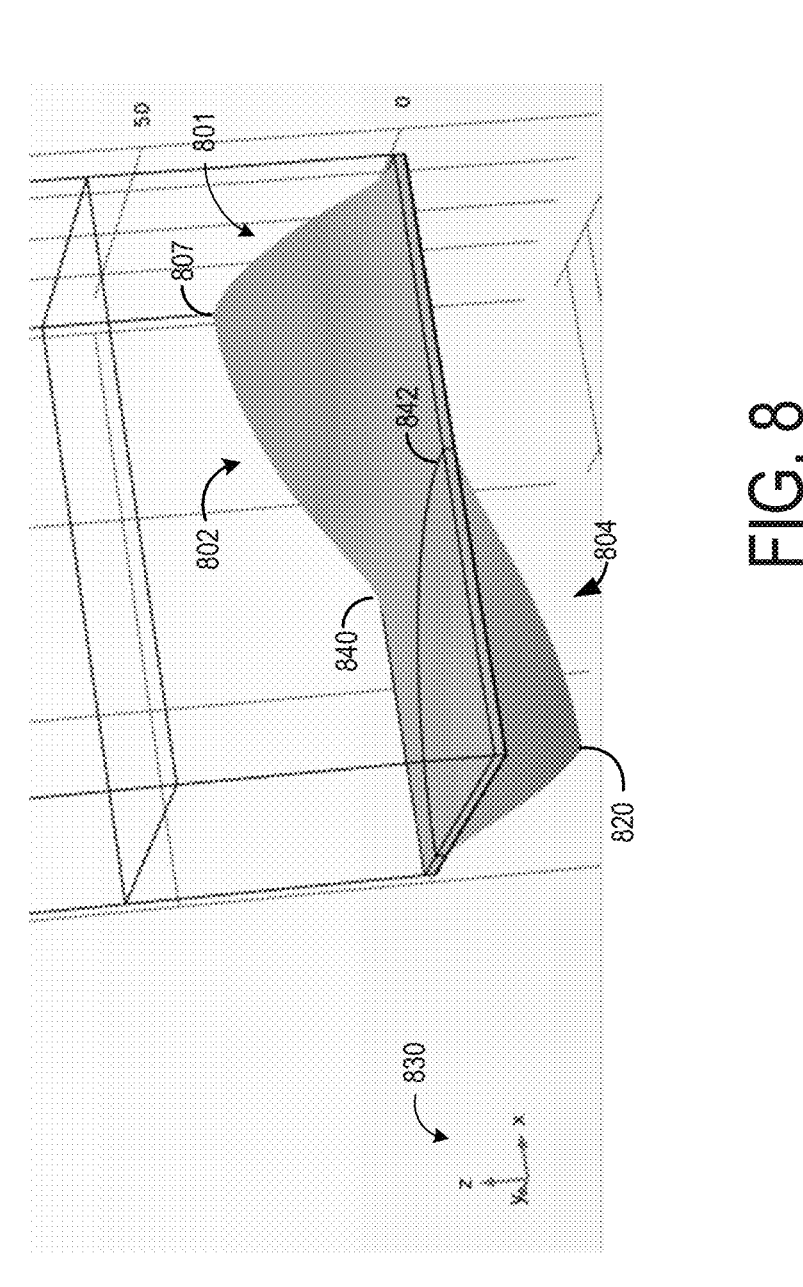
FIG. 8 shows a visualization of destructive interference between two transfer functions, in accordance with one or more embodiments of the present disclosure.

Referring briefly to FIG. 8, a three-dimensional (3D) visualization 800 of the destructive interference shows a membrane displacement in a z dimension, in accordance with reference axes 830, corresponding to two cMUTs of the plurality of cMUTs, including a first cMUT of the first portion and a second cMUT of the second portion. Specifically, 3D visualization 800 shows a first membrane 802 (quarter geometry) of a first cMUT of the first portion and a second membrane 804 of a second cMUT of the second portion of a same transducer element vibrating out of phase. This means the two membranes 802 and 804 at that frequency are vibrating with their corresponding displacement amplitudes, but in opposite directions, thereby cancelling a cumulative effect. This is visible as the notch-abyss in transmit sensitivity graph 600 of FIG. 6. First membrane 802 rises to a peak 807 in a positive direction along the z axis, where a first vibration of membrane 802 is strongest at a center of the first cMUT, and weakest at an edge of the first cMUT (e.g., at a point 840). Similarly, second membrane 804 descends to a peak 820 in a negative direction along the z axis, where a second vibration of membrane 804 is strongest at a center of the second cMUT, and weakest at an edge of the second cMUT indicated by a curved line 842.

FIG. 7 shows a third transmit sensitivity graph 700 of a combined acoustic signal 702 generated by the plurality of cMUTs of FIG. 5, with the mixed-bias configuration of FIG. 6, where the coupling layer has been added to reduce the destructive interference. The bias voltage of 90% of the collapse voltage is applied to the first portion of the plurality of cMUTs, and the bias voltage of 70% of the collapse voltage is applied to the second portion of the plurality of cMUTs. In FIG. 7, notch 605 of FIG. 6 that was caused by the destructive interference between the first transmit transfer function and the second transmit transfer function has been damped to smoothen the combined transmit transfer function and/or increase the frequency band of interest.

As a result of damping the destructive interference, acoustic signal 702 peaks at a point 704, corresponding to a maximum sensitivity of roughly 93 dB, as indicated by dashed line 706. Notch 620 of FIG. 6 has been reduced to a trough 720. A second dashed line 708 indicates a 3 dB decrease in sensitivity from the maximum sensitivity indicated by point 704. Thus, a fractional bandwidth 718 of acoustic signal 702 may be calculated by measuring a frequency range between a lowest frequency (fL) indicated by a first point 714 where second dashed line 708 intersects with acoustic signal 702, and a highest frequency (fH) indicated by a second point 716 where second dashed line 708 intersects with acoustic signal 702. In third transmit sensitivity graph 700, fL is 12.4 MHz, and fH is 26.6 MHz, where fractional bandwidth 718 is approximately 73%. Thus, fractional bandwidth 718 based on the mixed-bias configuration represents a 19% increase over fractional bandwidth 518 based on the homogenous bias used for the two portions of the cMUTs shown in FIG. 5.

It should be appreciated that while bandwidths 518 and 718 are 3 dB bandwidths, other reference dB values may be used in other embodiments. For example, bandwidths 518 and 718 may be calculated based on a 1 dB reduction from a peak value, or a 6 dB reduction from the peak value, or in a different manner, without affecting a relative difference between fractional bandwidth 518 of FIG. 5 and fractional bandwidth 718 of FIG. 7.

In this way, by applying different DC bias voltages to different groupings of cMUTs within transducer elements of a plurality of transducer elements of an ultrasound probe, the different groupings of cMUTs may resonate at different frequencies when an AC drive signal is applied, resulting in constructive interference of their corresponding transfer functions. The interference may be advantageously used to increase a fractional bandwidth of a combined acoustic signal generated by the different groupings of cMUTs. The increase in fractional bandwidth can be achieved by mixing and matching various optimized bias ratios, owing to the flexibility of using different cMUTs in carefully chosen resonance peak frequencies through varied levels of spring softening conditions. For example, in the example shown in FIGS. 5-7, the target design is a resonance frequency of approximately 20 MHz (fluid loaded) with a transmit fractional bandwidth of at least 70%. In the conventional case (e.g., FIG. 5), where 80% of the collapse voltage was used for both groupings, a fractional bandwidth of 51% was achieved. In the mixed-bias case, where 90% and 70% of the collapse voltage was used for the two groupings, a 73% fractional bandwidth was achieved. This optimum DC bias ratio of 70/90 was used to fix the resonance frequency at the 20 MHz level, and to ensure that the difference in amplitude represented by a height of notch 605 of FIG. 6 (e.g., between 604 and 620) is small enough to be damped by the coupling layer. In other words, an optimized DC bias ratio may be selected for a specific case where the constructive interference is large enough to maximize the fractional bandwidth, while the destructive interference (notch 605) remains small enough to be damped by the coupling layer.

By increasing the fractional bandwidth of the acoustic signals, a fractional bandwidth constraint imposed on higher-frequency ultrasound applications by a current membrane thickness may be removed, reducing a reliance on thinner and more costly membranes. The proposed method can be used in both lower- and higher-frequency high bandwidth applications. As a result, a single ultrasound probe that relies on the mixed-bias approach described herein may be used for a wider variety of clinical tasks than would otherwise be accomplished by various probes. By using the single ultrasound probe for the wider variety of clinical tasks, a cost of the ultrasound system may be reduced, and an efficiency of a workflow of a radiologist may be increased.

An additional advantage of applying the different DC bias voltages to different groupings of cMUTs within transducer elements of the plurality of transducer elements of an ultrasound probe is that a first grouping may be configured with a first DC bias voltage to transmit an acoustic signal, and a second grouping may be configured with a second DC voltage to receive an acoustic signal (e.g., reflected back from a patient).

A first technical effect of applying different DC bias voltages to different groups of cMUTs within transducer elements of a transducer array is that the different groups of cMUTs may be configured to resonate at different resonance frequencies when an AC drive signal is applied, which may interfere such that a fractional bandwidth of an acoustic signal generated by the transducer array may be increased, allowing the transducer array to be used for a wider selection of both low frequency and high frequency applications.

The disclosure also provides support for a method for an ultrasound system, the method comprising: during an ultrasound scan of a patient: during a transmit mode of a transducer element of a transducer array of an ultrasound probe of the ultrasound system: applying a first DC bias voltage to a first portion of capacitive micromachined ultrasound transducers (cMUTs) of the transducer element, applying a second DC bias voltage to a second portion of cMUTs of the transducer element, the second DC bias voltage different from the first DC bias voltage, applying an AC drive signal to the first portion of cMUTs to generate a first acoustic signal based on a first combination of the first DC bias voltage and the AC drive signal, causing membranes of the first portion of cMUTs to vibrate at a first resonance frequency defined by the first DC bias voltage, applying the AC drive signal to the second portion of cMUTs to generate a second acoustic signal based on a second combination of the second DC bias voltage and the AC drive signal, the second combination causing membranes of the second portion of cMUTs to vibrate at a second resonance frequency defined by the second DC bias voltage, the second resonance frequency different from the first resonance frequency by a threshold difference, and combining the first acoustic signal and the second acoustic signal to generate a higher-bandwidth signal, the higher-bandwidth signal based on constructive interference between a first transmit transfer function of the first portion of cMUTs and a second transmit transfer function of the second portion of cMUTs. In a first example of the method, the method further comprises: during a receive mode of the transducer element: receiving a second acoustic signal reflected from a scanned subject at both of the first portion of cMUTs and the second portion of cMUTs, generating a wider bandwidth output electrical signal based on constructive interference between a first receive transfer function generated at the first portion of cMUTs based on the first DC bias voltage and a second receive transfer function generated at the second portion of cMUTs based on the first DC bias voltage. In a second example of the method, optionally including the first example, the first portion of cMUTs are electrically coupled to a first bias voltage pad of the transducer element, and the first DC bias voltage is applied to the first portion of cMUTs via the first bias voltage pad, the second portion of cMUTs are electrically coupled to a second bias voltage pad of the transducer element, and the second DC bias voltage is applied to the second portion of cMUTs via the second bias voltage pad. In a third example of the method, optionally including one or both of the first and second examples, the first portion of cMUTs and the second portion of cMUTs are bundled through a back side of a wafer of the transducer array with through-wafer via connections. In a fourth example of the method, optionally including one or more or each of the first through third examples, the transducer array comprises a single transducer element. In a fifth example of the method, optionally including one or more or each of the first through fourth examples, the transducer array comprises a plurality of transducer elements, each transducer element of the plurality of transducer elements including at least the first bias voltage pad and the second bias voltage pad. In a sixth example of the method, optionally including one or more or each of the first through fifth examples, the method further comprises: applying the first DC bias voltage to a first plurality of first bias voltage pads of the plurality of transducer elements, and applying the second DC bias voltage to a second plurality of second bias voltage pads of the plurality of transducer elements. In a seventh example of the method, optionally including one or more or each of the first through sixth examples, the method further comprises: applying additional bias voltages to additional bias voltage pads of each transducer element, the additional bias voltage pads electrically coupled to additional, different portions of cMUTs of a respective transducer element. In a eighth example of the method, optionally including one or more or each of the first through seventh examples, the transducer array is one of a one-dimensional (1D) transducer array comprising a row of transducer elements, and a two-dimensional (2D) transducer array comprising a 2D matrix of transducer elements. In a ninth example of the method, optionally including one or more or each of the first through eighth examples, the method further comprises: dampening frequency transitions in the higher-bandwidth signal via a coupling layer covering the first portion of cMUTs and the second portion of cMUTs, the frequency transitions originating from destructive interference between a first transfer function based on the first DC bias voltage and a second transfer function based on the second DC bias voltage. In a tenth example of the method, optionally including one or more or each of the first through ninth examples, a fractional bandwidth of the higher-bandwidth signal is based on an optimized ratio of the first DC bias voltage to the second DC bias voltage, the optimized ratio maximizing the constructive interference of the higher-bandwidth signal, while maintaining the destructive interference small enough to be damped by the coupling layer. In a eleventh example of the method, optionally including one or more or each of the first through tenth examples, the method further comprises: using the ultrasound probe for both low and high frequency ultrasound applications.

The disclosure also provides support for an ultrasound system, comprising: an ultrasound probe including a transducer array comprising at least one transducer element, the at least one transducer element including a first portion of capacitive micromachined ultrasound transducers (cMUTs) electrically coupled to a first bias voltage pad of the at least one transducer element, and a second portion of cMUTs electrically coupled to a second bias voltage pad of the at least one transducer element, a processor, and a non-transitory memory including instructions that when executed, cause the processor to: during a transmit mode of the at least one transducer element: apply a first DC bias voltage to the first portion of cMUTs of the at least one transducer element, apply a second DC bias voltage to the second portion of cMUTs of the at least one transducer element, the second DC bias voltage different from the first DC bias voltage, apply an AC drive signal to the first portion of cMUTs to generate a first acoustic signal based on a first combination of the first DC bias voltage and the AC drive signal, causing membranes of the first portion of cMUTs to vibrate at a first resonance frequency defined by the first DC bias voltage, apply the AC drive signal to the second portion of cMUTs to generate a second acoustic signal based on a second combination of the second DC bias voltage and the AC drive signal, the second combination causing membranes of the second portion of cMUTs to vibrate at a second resonance frequency defined by the second DC bias voltage, the second resonance frequency different from the first resonance frequency by a threshold difference, and combine the first acoustic signal and the second acoustic signal to generate a higher-bandwidth signal, the higher-bandwidth signal based on constructive interference between a first transmit transfer function of the first portion of cMUTs and a second transmit transfer function of the second portion of cMUTs. In a first example of the system, further instructions are stored in the non-transitory memory that when executed, cause the processor to: during a receive mode of the at least one transducer element: receive a second acoustic signal reflected from a scanned subject at both of the first portion of cMUTs and the second portion of cMUTs, generate a wider bandwidth output electrical signal based on constructive interference between a first receive transfer function generated at the first portion of cMUTs based on the first DC bias voltage and a second receive transfer function generated at the second portion of cMUTs based on the first DC bias voltage. In a second example of the system, optionally including the first example, the transducer array comprises a plurality of transducer elements, and further instructions are stored in the non-transitory memory that when executed, cause the processor to apply the first DC bias voltage to each first bias voltage pad of each transducer element of the plurality of transducer elements, and apply the second DC bias voltage to each second bias voltage pad of each transducer element of the plurality of transducer elements. In a third example of the system, optionally including one or both of the first and second examples, further instructions are stored in the non-transitory memory that when executed, cause the processor to apply additional bias voltages to additional bias voltage pads of each transducer element, the additional bias voltage pads electrically coupled to additional, different portions of CMUTs of a respective transducer element. In a fourth example of the system, optionally including one or more or each of the first through third examples, the system further comprises: a coupling layer included between at least the first portion of cMUTs and the second portion of cMUTs of the at least one transducer element, that dampen frequency transitions originating from destructive interference between a first transfer function of the first DC bias voltage and a second transfer function of the second DC bias voltage. In a fifth example of the system, optionally including one or more or each of the first through fourth examples, a fractional bandwidth of the higher-bandwidth signal is based on an optimized ratio of the first DC bias voltage to the second DC bias voltage, the optimized ratio maximizing the constructive interference of the higher-bandwidth signal, while maintaining the destructive interference small enough to be damped by the coupling layer.

The disclosure also provides support for a method for an ultrasound system, the method comprising: during an ultrasound scan of a subject: applying a first DC bias voltage to a first portion of capacitive micromachined ultrasound transducers (cMUTs) of a transducer element of a transducer array of an ultrasound probe of the ultrasound system, the first DC bias voltage greater than a collapse voltage of the first portion of cMUTs, applying a second DC bias voltage to a second portion of cMUTs of the transducer element, the second DC bias voltage less than the collapse voltage of the second portion of cMUTs, applying an AC drive signal to the first portion of cMUTs to generate a first acoustic signal based on a first combination of the first DC bias voltage and the AC drive signal, causing membranes of the first portion of cMUTs to vibrate at a first resonance frequency based on the first DC bias voltage, receiving a second, reflected acoustic signal at the second portion of cMUTs, generating an electrical signal based on membranes of the second portion of cMUTs vibrating at a second resonance frequency based on the second DC bias voltage applied to the second portion of cMUTs, the second resonance frequency different from the first resonance frequency, and generating an ultrasound image based on the electrical signal. In a first example of the method, the first DC bias voltage is less than the collapse voltage, and the second DC bias voltage is greater than the collapse voltage.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound system, comprising:
an ultrasound probe including a transducer array comprising at least one transducer element, the at least one transducer element including a first portion of capacitive micromachined ultrasound transducers (cMUTs) electrically coupled to a first bias voltage pad of the at least one transducer element, and a second portion of cMUTs electrically coupled to a second bias voltage pad of the at least one transducer element, wherein the first bias voltage pad and the second bias voltage pad are separate bias voltage pads housed within the at least one transducer element;
a processor; and
a non-transitory memory including instructions that when executed, cause the processor to:
during a transmit mode of the at least one transducer element:
apply a first DC bias voltage to the first portion of cMUTs of the at least one transducer element;
apply a second DC bias voltage to the second portion of cMUTs of the at least one transducer element, the second DC bias voltage different from the first DC bias voltage, wherein a ratio between the first DC bias voltage and the second DC bias voltage is selected to maximize constructive interference while maintaining destructive interference at a level small enough to be damped by a coupling layer;
apply an AC drive signal to the first portion of cMUTs to generate a first acoustic signal based on a first combination of the first DC bias voltage and the AC drive signal, causing membranes of the first portion of cMUTs to vibrate at a first resonance frequency defined by the first DC bias voltage;
apply the AC drive signal to the second portion of cMUTs to generate a second acoustic signal based on a second combination of the second DC bias voltage and the AC drive signal, the second combination causing membranes of the second portion of cMUTs to vibrate at a second resonance frequency defined by the second DC bias voltage, the second resonance frequency different from the first resonance frequency by a threshold difference; and
combine the first acoustic signal and the second acoustic signal to generate a higher-bandwidth signal, the higher-bandwidth signal based on constructive interference between a first transmit transfer function of the first portion of cMUTs and a second transmit transfer function of the second portion of cMUTs.

2. The ultrasound system of claim 1, wherein further instructions are stored in the non-transitory memory that when executed, cause the processor to:

during a receive mode of the at least one transducer element:

receive a second acoustic signal reflected from a scanned subject at both of the first portion of cMUTs and the second portion of cMUTs;

generate a wider bandwidth output electrical signal based on constructive interference between a first receive transfer function generated at the first portion of cMUTs based on the first DC bias voltage and a second receive transfer function generated at the second portion of cMUTs based on the first DC bias voltage.

3. The ultrasound system of claim 1, wherein the transducer array comprises a plurality of transducer elements, and further instructions are stored in the non-transitory memory that when executed, cause the processor to apply the first DC bias voltage to each first bias voltage pad of each transducer element of the plurality of transducer elements, and apply the second DC bias voltage to each second bias voltage pad of each transducer element of the plurality of transducer elements.

4. The ultrasound system of claim 1, wherein further instructions are stored in the non-transitory memory that when executed, cause the processor to apply additional bias voltages to additional bias voltage pads of each transducer element, the additional bias voltage pads electrically coupled to additional, different portions of cMUTs of a respective transducer element.

5. The ultrasound system of claim 1, further comprising a coupling layer included between at least the first portion of cMUTs and the second portion of cMUTs of the at least one transducer element, that dampen frequency transitions originating from destructive interference between a first transfer function of the first DC bias voltage and a second transfer function of the second DC bias voltage.

6. The ultrasound system of claim 5, wherein a fractional bandwidth of the higher-bandwidth signal is based on an optimized ratio of the first DC bias voltage to the second DC bias voltage, the optimized ratio maximizing the constructive interference of the higher-bandwidth signal, while maintaining the destructive interference small enough to be damped by the coupling layer.

* * * * *